(12) United States Patent
Yeh et al.

(10) Patent No.: US 11,523,767 B2
(45) Date of Patent: Dec. 13, 2022

(54) SYSTEM, METHOD, AND COMPUTER PROGRAM PRODUCT FOR DETECTING NEURODEGENERATION USING DIFFERENTIAL TRACTOGRAPHY

(71) Applicant: University of Pittsburgh—Of the Commonwealth System of Higher Education, Pittsburgh, PA (US)

(72) Inventors: Fang-Cheng Yeh, Pittsburgh, PA (US); Robert Max Friedlander, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/160,433

(22) Filed: Jan. 28, 2021

(65) Prior Publication Data
US 2021/0228143 A1 Jul. 29, 2021

Related U.S. Application Data

(60) Provisional application No. 62/966,636, filed on Jan. 28, 2020.

(51) Int. Cl.
*G01V 3/00* (2006.01)
*A61B 5/00* (2006.01)
(Continued)

(52) U.S. Cl.
CPC .......... *A61B 5/4082* (2013.01); *A61B 5/0042* (2013.01); *A61B 5/055* (2013.01);
(Continued)

(58) Field of Classification Search
CPC ............. G01R 33/3415; G01R 33/543; G01R 33/5659; G01R 33/36; A61B 5/055
(Continued)

(56) References Cited

U.S. PATENT DOCUMENTS

2008/0284434 A1* 11/2008 Wedeen ........... G01R 33/56341
324/309
2009/0016590 A1 1/2009 Tseng et al.
(Continued)

OTHER PUBLICATIONS

Neuroscience.pdf (Year: 2021).*
(Continued)

*Primary Examiner* — Walter L Lindsay, Jr.
*Assistant Examiner* — Frederick Wenderoth
(74) *Attorney, Agent, or Firm* — The Webb Law Firm

(57) ABSTRACT

Described are a system, method, and computer program product for detecting neurodegeneration using differential tractography and treating neurological disorders accordingly. The method includes obtaining a first diffusion magnetic resonance imaging (MRI) scan of the brain of the patient and obtaining a plurality of diffusion MRI scans of a group of other brains. The method also includes generating a control diffusion MRI scan based on the plurality of diffusion MRI scans of the group of other brains. The method further includes determining a first anisotropy of first neural tracks of the first diffusion MRI scan and a second anisotropy of second neural tracks of the control diffusion MRI scan. The method further includes determining a differential by comparing the first anisotropy to the second anisotropy and identifying at least one neurological disorder based on the differential and a location of the first neural tracks in the brain of the patient.

21 Claims, 20 Drawing Sheets
(16 of 20 Drawing Sheet(s) Filed in Color)

(51) Int. Cl.

| | | |
|---|---|---|
| *A61B 5/055* | (2006.01) | |
| *G01R 33/563* | (2006.01) | |
| *G01R 33/56* | (2006.01) | |
| *G16H 30/40* | (2018.01) | |
| *G16H 50/20* | (2018.01) | |
| *G16H 20/70* | (2018.01) | |
| *G06T 7/00* | (2017.01) | |

(52) U.S. Cl.
CPC ... *G01R 33/5608* (2013.01); *G01R 33/56341* (2013.01); *G06T 7/0014* (2013.01); *G16H 20/70* (2018.01); *G16H 30/40* (2018.01); *G16H 50/20* (2018.01); *A61B 2576/026* (2013.01); *G06T 2207/10088* (2013.01); *G06T 2207/30016* (2013.01)

(58) Field of Classification Search
USPC .......................................................... 324/309
See application file for complete search history.

(56) References Cited

U.S. PATENT DOCUMENTS

| | | | |
|---|---|---|---|
| 2010/0253337 A1 | 10/2010 | Tseng et al. | |
| 2011/0181284 A1* | 7/2011 | Balcom ................... | G01R 33/58 324/309 |
| 2011/0288400 A1* | 11/2011 | Russell ................ | A61B 5/0035 600/411 |
| 2013/0259340 A1 | 10/2013 | Tseng et al. | |
| 2015/0198688 A1* | 7/2015 | Cetingul .......... | G01R 33/56341 324/309 |
| 2019/0142964 A1* | 5/2019 | Rangaramanujam ....................... | C08G 83/004 424/179.1 |
| 2020/0380740 A1 | 12/2020 | Yeh et al. | |

OTHER PUBLICATIONS

Abhinav et al., "Use of diffusion spectrum imaging in preliminary longitudinal evaluation of amyotrophic lateral sclerosis: development of an imaging biomarker". Frontiers in Human Neuroscience, Apr. 2014, pp. 1-11, vol. 8:270.
Basser et al., "Estimation of the Effective Self-Diffusion Tensor from the NMR Spin Echo", Journal of Magnetic Resonance, Series B,1994, pp. 247-254, vol. 103.
Budde et al., "Axial Diffusivity Is the Primary Correlate of Axonal Injury in the Experimental Autoimmune Encephalomyelitis Spinal Cord: A Quantitative Pixelwise Analysis", The Journal of Neuroscience, Mar. 4, 2009, pp. 2805-2813, vol. 29:9.
Filippini et al., "Corpus callosum involvement is a consistent feature of amyotrophic lateral sclerosis", Neurology, 2010, pp. 1645-1652, vol. 75.
Glasser et al.,"The Human Connectome Project's neuroimaging approach", Nature Neuroscience, Sep. 2016, pp. 1175-1187, vol. 19:9.
Henf et al., "Mean diffusivity in cortical gray matter in Alzheimer's disease: The importance of partial volume correction", NeuroImage: Clinical, 2017, pp. 1-27.
Huisman et al., "Diffusion Tensor Imaging as Potential Biomarker of White Matter Injury in Diffuse Axonal Injury", AJNR Am J Neuroradiol, Mar. 2004, pp. 370-376, vol. 25.
Loewe et al., "Widespread temporo-occipital lobe dysfunction in amyotrophic lateral sclerosis", Scientific Reports, 2017, pp. 1-9, vol. 7:40252.
Maier-Hein, "The challenge of mapping the human connectome based on diffusion fractography", Nature Communications, 2017, pp. 1-13, vol. 8:1349.

Maroon et al. "Rewiring the Brain: Connectomics, Neuro Epigenetics and Neuroplasticity", Department of Neurosurgery, Presentation given at A4M in Las Vegas, Nevada, Dec. 2018, 56 pages.
Melonakos et al., "Voxel-based morphometry (VBM) studies in schizophrenia—can white matter changes be reliably detected with VBM?", Psychiatry Research: Neuroimaging, 2011, pp. 65-70, vol. 193.
Roosendaal et al., "Regional DTI differences in multiple sclerosis patients", NeuroImage, 2009, pp. 1397-1403, vol. 44.
Rovira et al., "MAGNIMS consensus guidelines on the use of MRI in multiple sclerosis—clinical implementation in the diagnostic process", Nature Reviews: Neurology, 2015, pp. 1-12.
Sanchez-Castaneda et al., "Seeking Huntington Disease Biomarkers by Multimodal, Cross-Sectional Basal Ganglia Imaging", Human Brain Mapping, 2012, pp. 1-11.
Schilling et al., "A fiber coherence index for quality control of B-table orientation in diffusion MRI scans", Magnetic Resonance Imaging, 2019, pp. 82-89, vol. 58.
Song et al., "Dysmyelination Revealed through MRI as Increased Radial (but Unchanged Axial) Diffusion of Water", NeuroImage, 2002, pp. 1429-1436, vol. 17.
Song et al., "Demyelination increases radial diffusivity in corpus callosum of mouse brain", NeuroImage, 2005, pp. 132-140, vol. 26.
Sydykova et al., "Fiber Connections between the Cerebral Cortex and the Corpus Callosum in Alzheimer's Disease: A Diffusion Tensor Imaging and Voxel-Based Morphometry Study", Cerebral Cortex, Oct. 2007, pp. 2276-2282, vol. 17.
Tabrizi et al., "Biological and clinical manifestations of Huntington's disease in the longitudinal TRACK-HD study: cross-sectional analysis of baseline data", Lancet Neurol, Sep. 2009, pp. 791-801, vol. 8.
Tabrizi et al., "Potential endpoints for clinical trials in premanifest and early Huntington's disease in the TRACK-HD study: analysis of 24 month observational data", Lancet Neurol, Jan. 2012, pp. 42-52, vol. 11.
Wang et al., "Quantification of increased cellularity during inflammatory demyelination", Brain: A Journal of Neurology, 2011, pp. 3590-3601, vol. 134.
Wattjes et al., MAGNIMS consensus guidelines on the use of MRI in multiple sclerosis—establishing disease prognosis and monitoring patients, Nature Reviews: Neurology, 2015, pp. 1-10.
Wedeen et al., "The Geometric Structure of the Brain Fiber Pathways", Science, Mar. 30, 2012, pp. 1628-1634, vol. 335.
Werring et al., "Diffusion tensor imaging of lesions and normal-appearing white matter in multiple sclerosis", Neurology, May 1, 1999, 20 pages, vol. 52:8.
Werring et al., "Diffusion tensor imaging can detect and quantify corticospinal tract degeneration after stroke", J Neurol Neurosurg Psychiatry, 2000, pp. 269-272, vol. 69.
Woo et al., "Cluster-extent based thresholding in fMRI analyses: Pitfalls and recommendations", NeuroImage, 2014, pp. 412-419, vol. 91.
Yeh et al., "Generalized q-Sampling Imaging", IEEE Transactions on Medical Imaging, Sep. 2010, pp. 1626-1635, vol. 29:9.
Yeh et al., "NTU-90: A high angular resolution brain atlas constructed by q-space diffeomorphic reconstruction", NeuroImage, 2011, pp. 91-99, vol. 58.
Yeh et al., "Deterministic Diffusion Fiber Tracking Improved by Quantitative Anisotropy", Plos One, Nov. 2013, pp. 1-16, vol. 8:11.
Yeh et al., Quantifying Differences and Similarities in Whole-Brain White Matter Architecture Using Local Connectome Fingerprints, PLOS Computational Biology, Nov. 15, 2016, pp. 1-17.
Yeh et al., Automatic Removal of False Connections in Diffusion MRI Tractography Using Topology-Informed Pruning (TIP), Neurotherapeutics, 2018, pp. 1-7.
Zhang et al., "Occipital cortical gyrification reductions associate with decreased functional connectivity in amyotrophic lateral sclerosis", Brain Imaging and Behavior, 2016, pp. 1-7.

\* cited by examiner

| | diagnosis | age | sex | MRI scans | major symptoms |
|---|---|---|---|---|---|
| #1 | multiple sclerosis | 44 | F | onset of symptom and 6-month follow-up | acute onset of left ocular pain, pain with eye movements, blurring vision of the left eye (20/400), loss of visual field in all quadrants. |
| #2 | multiple sclerosis | 24 | F | onset of symptom and 6-month follow-up | acute onset of left ocular pain, pain with eye movements, blurring vision of the right eye (20/125), superior altitudinal visual field defect. |
| #3 | Huntington's disease | 60 | M | two scans at 5 months apart during the manifest stage | body bradykinesia on both sides UHDRS motor: 45 → 49 (worsening) |
| #4 | Huntington's disease | 55 | F | two scans at 5 months apart during the manifest stage | dystonia of left upper extremity, dragging right foot with ambulation, dystonia of the right leg UHDRS motor: 53 → 64 (worsening) |
| #5 | ALS | 48 | M | baseline scan acquired 30 months after onset follow-up scan acquired one year after. | left-hand weakness with fasciculations ALSFRS-R: 45 → 32 (worsening) |
| #6 | epilepsy | 51 | M | before anterior temporal lobectomy and one-year follow-up after surgery | |

*FIG. 2*

| Sub-ject | Scan | Manifest/Pre-manifest | Cingulum Volume (mm³) | Corpus Callosum Volume (mm³) | Cortico-striatal Pathway Volume (mm³) | Cortico-spinal Pathway Volume (mm³) | Whole Brain Volume (mm³) |
|---|---|---|---|---|---|---|---|
| A | 1 | Manifest | 760 | 6032 | 4736 | 2224 | 15103 |
|   | 2 |   | 824 | 5360 | 5432 | 2040 | 17878 |
|   | 3 |   | 1176 | 21152 | 8176 | 17112 | 39588 |
| B | 1 | Manifest | 1872 | 13336 | 0 | 19816 | 33236 |
|   | 2 |   | 4120 | 35296 | 6352 | 21992 | 61214 |
|   | 3 |   | 2656 | 26688 | 3096 | 26096 | 51240 |
| C | 1 | Manifest | 952 | 5248 | 968 | 15944 | 16502 |
|   | 2 |   | 1312 | 21168 | 3624 | 37496 | 56512 |
|   | 3 |   | 2096 | 23304 | 6440 | 39296 | 64686 |
| D | 1 | Manifest | 0 | 0 | 0 | 0 | 5917 |
|   | 2 |   | 0 | 0 | 520 | 0 | 6323 |
|   | 3 |   | 0 | 3184 | 752 | 0 | 10370 |
| E | 1 | Manifest | 3080 | 40032 | 4832 | 36200 | 77794 |
|   | 2 |   | 5768 | 41640 | 608 | 31272 | 80894 |
| F | 1 | Manifest | 408 | 5872 | 688 | 1512 | 11690 |
|   | 2 |   | 0 | 0 | 1048 | 1176 | 6413 |
|   | 3 |   | 0 | 0 | 1352 | 0 | 5664 |
| G | 1 | Manifest | 1608 | 41504 | 1896 | 43168 | 87789 |
| H | 1 | Manifest | 37064 | 37064 | 13280 | 44872 | 119938 |

*FIG. 7A*

| Subject | Scan | Manifest/ Pre-manifest | Cingulum Volume (mm³) | Corpus Callosum Volume (mm³) | Cortico-striatal Pathway Volume (mm³) | Cortico-spinal Pathway Volume (mm³) | Whole Brain Volume (mm³) |
|---|---|---|---|---|---|---|---|
| I | 1 | Premanifest | 280 | 9144 | 7336 | 36184 | 55752 |
|   | 2 |  | 0 | 1216 | 0 | 0 | 3769 |
|   | 3 |  | 0 | 1984 | 664 | 2680 | 6223 |
| J | 1 | Manifest | 0 | 19352 | 4176 | 1736 | 23829 |
|   | 2 |  | 1232 | 52248 | 9672 | 42800 | 97512 |
|   | 3 |  | 1856 | 35184 | 8168 | 16608 | 60167 |
| K | 1 | Manifest | 592 | 9904 | 1776 | 14976 | 27213 |
|   | 2 |  | 2808 | 48720 | 3480 | 43592 | 91088 |
|   | 3 |  | 2104 | 28136 | 7944 | 28216 | 58704 |
| L | 1 | Premanifest | 0 | 0 | 0 | 280 | 130 |
| M | 1 | Premanifest | 0 | 272 | 840 | 5480 | 9763 |
|   | 2 |  | 0 | 0 | 0 | 0 | 0 |
|   | 3 |  | 0 | 0 | 0 | 0 | 0 |
| N | 1 | Premanifest | 0 | 0 | 224 | 3328 | 5059 |
|   | 2 |  | 0 | 0 | 0 | 1192 | 2961 |
|   | 3 |  | 816 | 4864 | 3464 | 17336 | 22114 |
| O | 1 | Manifest | 496 | 32096 | 8696 | 26536 | 60015 |
|   | 2 |  | 560 | 41472 | 12128 | 32992 | 67966 |
|   | 3 |  | 2608 | 66248 | 22800 | 56328 | 137436 |
| P | 1 | Manifest | 592 | 712 | 1816 | 656 | 7210 |
|   | 2 |  | 0 | 3976 | 3664 | 1464 | 10892 |
|   | 3 |  | 2344 | 34240 | 7416 | 10920 | 51041 |

*FIG. 7B*

|  | Clinical scores | Correlation between clinical scores and tract volume | | | Correlation between change in clinical scores and change in tract volumes | | |
|---|---|---|---|---|---|---|---|
|  |  | coefficient | standard error | p-value | coefficient | standard error | p-value |
| Cingulum | UHDRS TMS | 0.088 | 0.018 | <.0001 | 0.380 | 0.403 | 0.173 |
|  | Dystonia total | 0.187 | 0.093 | 0.022 | 0.870 | 0.158 | <.0001 |
|  | Chorea total | -0.032 | 0.118 | 0.608 | -0.325 | 0.379 | 0.804 |
|  | RAM | 0.522 | 0.075 | <.0001 | 0.602 | 0.148 | <.0001 |
|  | Stroop Color Word | -0.115 | 0.029 | <.0001 | 0.032 | 0.216 | 0.559 |
|  | UHDRS Behavior | 0.081 | 0.055 | 0.067 | 0.317 | 0.132 | 0.008 |
|  | UHDRS TFC | 0.046 | 0.007 | <.0001 | -0.258 | 0.144 | 0.964 |
| Corpus Callosum | UHDRS TMS | 0.073 | 0.027 | 0.003 | 0.292 | 0.531 | 0.291 |
|  | Dystonia total | 0.259 | 0.089 | 0.002 | 1.170 | 0.267 | <.0001 |
|  | Chorea total | -0.030 | 0.163 | 0.572 | -0.980 | 0.455 | 0.984 |
|  | RAM | 0.438 | 0.124 | <.0001 | 2.746 | 0.251 | <.0001 |
|  | Stroop Color Word | -0.134 | 0.039 | <.0001 | 0.538 | 1.069 | 0.693 |
|  | UHDRS Behavior | 0.023 | 0.073 | 0.374 | -0.045 | 0.208 | 0.586 |
|  | UHDRS TFC | 0.033 | 0.013 | 0.005 | -0.405 | 0.130 | 0.999 |
| Corticostriatal Pathway | UHDRS TMS | 0.070 | 0.013 | <.0001 | 0.185 | 0.358 | 0.303 |
|  | Dystonia total | 0.305 | 0.132 | 0.011 | 0.337 | 0.228 | 0.070 |
|  | Chorea total | 0.058 | 0.097 | 0.276 | -0.663 | 0.369 | 0.964 |
|  | RAM | 0.420 | 0.073 | <.0001 | 2.587 | 0.279 | <.0001 |
|  | Stroop Color Word | -0.080 | 0.028 | 0.003 | 0.569 | 0.982 | 0.719 |
|  | UHDRS Behavior | -0.014 | 0.063 | 0.587 | -0.121 | 0.181 | 0.748 |
|  | UHDRS TFC | 0.030 | 0.007 | <.0001 | -0.071 | 0.074 | 0.831 |

Significant (p-value <0.05).

Extremely significant (p-value <0.0001).

UHDRS: Unified Huntington Disease Rating Scale. TMS: Total motor score. RAM: Rapid alternating movements. TFC: Total functional capacity.

FIG. 9A

|  | Clinical scores | Correlation between clinical scores and tract volume | | | Correlation between change in clinical scores and change in tract volumes | | |
| --- | --- | --- | --- | --- | --- | --- | --- |
|  |  | coefficient | standard error | p-value | coefficient | standard error | p-value |
| Corticospinal Pathway | UHDRS TMS | 0.054 | 0.025 | 0.015 | 0.288 | 0.396 | 0.234 |
|  | Dystonia total | 0.169 | 0.161 | 0.147 | 0.458 | 0.278 | 0.050 |
|  | Chorea total | -0.069 | 0.143 | 0.685 | -0.517 | 0.425 | 0.888 |
|  | RAM | 0.408 | 0.097 | <.0001 | 3.009 | 0.310 | <.0001 |
|  | Stroop Color Word | -0.105 | 0.044 | 0.009 | 0.814 | 1.130 | 0.764 |
|  | UHDRS Behavior | 0.028 | 0.069 | 0.344 | -0.131 | 0.217 | 0.728 |
|  | UHDRS TFC | 0.030 | 0.010 | 0.001 | -0.171 | 0.087 | 0.976 |
| Whole Brain | UHDRS TMS | 0.053 | 0.020 | 0.003 | 0.385 | 0.446 | 0.194 |
|  | Dystonia total | 0.145 | 0.058 | 0.006 | 0.560 | 0.301 | 0.031 |
|  | Chorea total | 0.083 | 0.072 | 0.123 | -0.548 | 0.441 | 0.893 |
|  | RAM | 0.293 | 0.097 | 0.001 | 3.249 | 0.309 | <.0001 |
|  | Stroop Color Word | -0.067 | 0.026 | 0.005 | 0.854 | 1.200 | 0.762 |
|  | UHDRS Behavior | -0.011 | 0.039 | 0.611 | -0.094 | 0.225 | 0.661 |
|  | UHDRS TFC | 0.021 | 0.007 | 0.002 | -0.206 | 0.101 | 0.980 |

Significant (p-value <0.05).

Extremely significant (p-value <0.0001).

UHDRS: Unified Huntington Disease Rating Scale. TMS: Total motor score. RAM: Rapid alternating movements. TFC: Total functional capacity.

FIG. 9B

|  |  | Correlation between clinical scores and tract volume | | | | | |
|---|---|---|---|---|---|---|---|
|  |  | First Scan | | Second Scan | | Third Scan | |
|  | Clinical scores | corr | p-value | corr | p-value | corr | p-value |
| Cingulum | UHDRS TMS | 0.345 | 0.136 | 0.735 | 0.012 | -0.042 | 0.543 |
|  | Dystonia total | -0.114 | 0.638 | 0.138 | 0.362 | -0.269 | 0.758 |
|  | Chorea total | -0.117 | 0.641 | 0.211 | 0.293 | -0.517 | 0.923 |
|  | RAM | -0.025 | 0.531 | 0.397 | 0.145 | 0.209 | 0.294 |
|  | Stroop C W | -0.500† | 0.049 | -0.046 | 0.453 | -0.343 | 0.183 |
|  | UHDRS Behavior | 0.004 | 0.496 | 0.312 | 0.207 | -0.025 | 0.526 |
|  | UHDRS TFC | 0.240 | 0.226 | 0.594 | 0.046 | 0.176 | 0.326 |
| Corpus Callosum | UHDRS TMS | -0.223 | 0.757 | 0.240 | 0.267 | -0.417 | 0.868 |
|  | Dystonia total | -0.253 | 0.786 | 0.160 | 0.340 | -0.698 | 0.982 |
|  | Chorea total | -0.246 | 0.780 | 0.101 | 0.398 | -0.343 | 0.817 |
|  | RAM | -0.495 | 0.949 | -0.034 | 0.534 | -0.119 | 0.620 |
|  | Stroop C W | -0.347 | 0.135 | 0.315 | 0.796 | -0.150 | 0.350 |
|  | UHDRS Behavior | 0.239 | 0.227 | 0.228 | 0.278 | 0.285 | 0.229 |
|  | UHDRS TFC | -0.012 | 0.515 | 0.042 | 0.457 | -0.433 | 0.878 |
| Corticostriatal Pathway | UHDRS TMS | -0.050 | 0.561 | -0.184 | 0.682 | -0.033 | 0.534 |
|  | Dystonia total | 0.027 | 0.467 | -0.023 | 0.523 | -0.213 | 0.709 |
|  | Chorea total | -0.042 | 0.552 | -0.563 | 0.943 | -0.251 | 0.743 |
|  | RAM | -0.412 | 0.909 | 0.042 | 0.457 | 0.111 | 0.388 |
|  | Stroop C W | 0.028 | 0.535 | -0.268 | 0.243 | -0.133 | 0.366 |
|  | UHDRS Behavior | 0.177 | 0.291 | 0.277 | 0.235 | 0.720 | 0.014 |
|  | UHDRS TFC | -0.071 | 0.586 | -0.150 | 0.650 | -0.100 | 0.601 |

▨ Significant (p-value <0.05).

▨ Strong correlation.

† Higher Stroop Color Word Score indicate better cognitive performance. Negative value does not indicate negative correlation.

FIG. 10A

|  |  | Correlation between clinical scores and tract volume | | | | | |
|---|---|---|---|---|---|---|---|
|  |  | First Scan | | Second Scan | | Third Scan | |
|  | Clinical scores | corr | p-value | corr | p-value | corr | p-value |
| Corticospinal Pathway | UHDRS TMS | 0.110 | 0.367 | 0.251 | 0.257 | 0.460 | 0.106 |
| | Dystonia total | -0.312 | 0.839 | 0.274 | 0.238 | 0.098 | 0.401 |
| | Chorea total | 0.032 | 0.461 | 0.345 | 0.182 | 0.046 | 0.453 |
| | RAM | -0.279 | 0.810 | -0.193 | 0.691 | 0.303 | 0.214 |
| | Stroop C W | -0.305 | 0.168 | 0.351 | 0.823 | -0.243 | 0.265 |
| | UHDRS Behavior | 0.165 | 0.304 | -0.101 | 0.602 | 0.193 | 0.309 |
| | UHDRS TFC | 0.090 | 0.391 | -0.133 | 0.634 | 0.243 | 0.265 |
| Whole Brain | UHDRS TMS | 0.046 | 0.444 | 0.251 | 0.257 | 0.067 | 0.432 |
| | Dystonia total | -0.382 | 0.890 | 0.160 | 0.341 | -0.289 | 0.775 |
| | Chorea total | 0.011 | 0.487 | 0.109 | 0.390 | 0.075 | 0.424 |
| | RAM | -0.348 | 0.867 | -0.025 | 0.526 | -0.017 | 0.517 |
| | Stroop C W | -0.273 | 0.196 | 0.268 | 0.757 | -0.150 | 0.350 |
| | UHDRS Behavior | 0.147 | 0.324 | 0.252 | 0.256 | 0.167 | 0.333 |
| | UHDRS TFC | 0.067 | 0.418 | 0.067 | 0.432 | -0.200 | 0.697 |

FIG. 10B

|  |  | Correlation between change in clinical scores and change in tract volumes | | | | | |
|---|---|---|---|---|---|---|---|
|  |  | Change 1st scan to 2nd scan | | Change: 1st to 3rd scan | | Change: 2nd to 3rd scan | |
|  | Clinical scores | corr | p-value | corr | p-value | corr | p-value |
| Cingulum | UHDRS TMS | 0.477 | 0.097 | -0.214 | 0.695 | 0.548 | 0.080 |
|  | Dystonia total | 0.602 | 0.043 | -0.400 | 0.837 | 0.115 | 0.393 |
|  | Chorea total | 0.128 | 0.371 | -0.539 | 0.916 | 0.445 | 0.135 |
|  | RAM | 0.375 | 0.160 | 0.528 | 0.089 | 0.358 | 0.192 |
|  | Stroop C W | 0.513 | 0.921 | -0.707† | 0.025 | 0.283 | 0.752 |
|  | UHDRS Behavior | 0.351 | 0.177 | 0.313 | 0.225 | 0.602 | 0.057 |
|  | UHDRS TFC | 0.427 | 0.126 | -0.238 | 0.715 | 0.645 | 0.042 |
| Corpus Callosum | UHDRS TMS | -0.067 | 0.568 | 0.071 | 0.433 | 0.335 | 0.208 |
|  | Dystonia total | 0.842 | 0.002 | -0.170 | 0.656 | 0.374 | 0.181 |
|  | Chorea total | -0.213 | 0.709 | -0.455 | 0.871 | 0.417 | 0.152 |
|  | RAM | -0.220 | 0.716 | 0.712 | 0.024 | -0.410 | 0.843 |
|  | Stroop C W | 0.234 | 0.728 | -0.503 | 0.102 | 0.755 | 0.985 |
|  | UHDRS Behavior | 0.367 | 0.166 | 0.386 | 0.173 | 0.096 | 0.411 |
|  | UHDRS TFC | -0.233 | 0.727 | -0.190 | 0.674 | 0.084 | 0.422 |
| Corticostriatal Pathway | UHDRS TMS | -0.400 | 0.857 | 0.071 | 0.433 | 0.036 | 0.466 |
|  | Dystonia total | 0.337 | 0.188 | -0.170 | 0.656 | -0.181 | 0.666 |
|  | Chorea total | -0.741 | 0.989 | -0.455 | 0.871 | -0.012 | 0.512 |
|  | RAM | -0.254 | 0.745 | 0.712 | 0.024 | 0.133 | 0.377 |
|  | Stroop C W | 0.025 | 0.526 | -0.503 | 0.102 | 0.419 | 0.849 |
|  | UHDRS Behavior | 0.183 | 0.318 | 0.386 | 0.173 | 0.431 | 0.143 |
|  | UHDRS TFC | -0.083 | 0.584 | -0.190 | 0.674 | 0.503 | 0.102 |

▨ Significant (*p-value* <0.05).

▨ Strong correlation.

† Higher Stroop Color Word Score indicate better cognitive performance. Negative value does not indicate negative correlation.

FIG. 10C

|  |  | Correlation between change in clinical scores and change in tract volumes | | | | | |
|---|---|---|---|---|---|---|---|
|  |  | Change 1st scan to 2nd scan | | Change: 1st to 3rd scan | | Change: 2nd to 3rd scan | |
|  | Clinical scores | corr | p-value | corr | p-value | corr | p-value |
| Corticospinal Pathway | UHDRS TMS | -0.483 | 0.906 | 0.238 | 0.285 | 0.048 | 0.455 |
| | Dystonia total | 0.614 | 0.039 | 0.012 | 0.489 | 0.410 | 0.157 |
| | Chorea total | -0.383 | 0.846 | -0.491 | 0.892 | -0.147 | 0.636 |
| | RAM | -0.576 | 0.948 | 0.589 | 0.062 | -0.711 | 0.976 |
| | Stroop C W | -0.008 | 0.492 | -0.132 | 0.378 | 0.539 | 0.916 |
| | UHDRS Behavior | 0.333 | 0.190 | 0.506 | 0.100 | -0.156 | 0.644 |
| | UHDRS TFC | -0.467 | 0.897 | 0.262 | 0.265 | -0.156 | 0.644 |
| Whole Brain | UHDRS TMS | -0.150 | 0.650 | 0.071 | 0.433 | 0.347 | 0.200 |
| | Dystonia total | 0.703 | 0.017 | -0.158 | 0.645 | 0.434 | 0.141 |
| | Chorea total | -0.179 | 0.677 | -0.419 | 0.849 | 0.209 | 0.310 |
| | RAM | -0.297 | 0.781 | 0.565 | 0.072 | -0.374 | 0.819 |
| | Stroop C W | 0.310 | 0.791 | -0.395 | 0.166 | 0.790 | 0.990 |
| | UHDRS Behavior | 0.483 | 0.094 | 0.422 | 0.149 | 0.096 | 0.411 |
| | UHDRS TFC | -0.083 | 0.584 | 0.071 | 0.433 | 0.192 | 0.325 |

▒ Significant (p-value <0.05).

▒ Strong correlation.

† Higher Stroop Color Word Score indicate better cognitive performance. Negative value does not indicate negative correlation.

FIG. 10D

SYSTEM, METHOD, AND COMPUTER PROGRAM PRODUCT FOR DETECTING NEURODEGENERATION USING DIFFERENTIAL TRACTOGRAPHY

CROSS-REFERENCE TO RELATED APPLICATION

This application claims priority to U.S. Provisional Patent Application No. 62/966,636, filed Jan. 28, 2020, the disclosure of which is incorporated by reference herein in its entirety.

STATEMENT REGARDING FEDERAL FUNDING

This invention was made with government support under Grant No. MH113634, awarded by the National Institutes of Health. The government has certain rights in the invention.

BACKGROUND

1. Field

This disclosure relates generally to neuroscience and, in non-limiting embodiments, bio-digital methods and systems for monitoring brain health, and uses thereof, including detecting and responding to neurodegeneration.

2. Technical Considerations

Neurodegenerative disorders are caused by structural and/or functional changes to neural pathways in a brain. Structural and/or functional changes to neural pathways may be present before outward symptoms manifest in a patient. The prognosis of a neurodegenerative disorder may be improved by early detection of the disorder, which may allow for earlier treatment. Earlier treatment may result in the slowing, halting, or reversing of the progression of neurodegeneration in a patient.

There is a need in the art for an improved system and method of accurately detecting neurodegeneration in a patient's brain, which may be used for diagnosis and/or treatment of neurodegenerative disorders.

SUMMARY

Diffusion magnetic resonance imagery (MRI) tractography has been used to show brain architecture in human subjects, but its ability to specify neuropathological change is limited. The current fiber tracking methods only show the existence of fiber tracks in human brain. Diffusion MRI has also been investigated to explore its role as an imaging biomarker for neurodegeneration, since studies have shown that the diffusion properties have substantial change during acute demyelination. Moreover, diffusion MRI data analyzed by diffusion tensor imaging (DTI) allows for in-vivo tracking of axonal fiber trajectories to reveal the tractography of white matter pathways that are otherwise not visible in structural MRI. These two existing applications suggest that diffusion MRI has the potential to serve as an imaging biomarker to reveal tracks with neurodegeneration. However, DTI fiber tracking only allows for finding the existence of an axonal connection and is insensitive to early neurodegeneration, and studies using DTI or its derived tractography only reveal local diffusivities change in group studies. A reliable and sensitive method to reveal the exact segment of fiber pathways affected by neurodegeneration is yet to be developed. The method described herein will show the exact part of tracks with neurodegeneration.

Here we introduce a novel tractography approach called differential tractography, which makes use of advanced MRI acquisitions to track only the segments of pathways with neurodegeneration as reflected by a decrease of anisotropic diffusion. This allows for enhanced identification of pathways with neurodegeneration that were otherwise not visible in conventional tractography. Combined with a sham setting, differential tractography further allows for statistically estimating the positive predictive value (PPV) of the findings to access their reliability. To evaluate the performance of differential tractography, we applied differential tractography to four different neurological disorders involving possible neurodegeneration, including multiple sclerosis patients with first episode of optic neuritis, manifested Huntington disease patients, a patient with amyotrophic lateral sclerosis (ALS), and an epileptic patient after anterior temporal lobectomy, aiming to examine the performance in early-stage neurodegeneration, progressive neurodegeneration, and established late-stage neurodegeneration, respectively.

Our results show that differential tractography can reveal the location and quantify the severity of neurodegeneration at three different stages of neurodegeneration and of neurodegeneration. The location and severity of neurodegeneration findings matched well with clinical symptoms and disease severity. By using an optimized anisotropy and length threshold, we can effectively achieve an estimated PPV of 97% without losing most of the findings. This novel approach enables a quantitative and objective approach to investigate the neurodegeneration in individuals, allowing for diagnostic and prognostic evaluation as well as assessing the treatment response.

According to a non-limiting embodiment or aspect, provided is a computer-implemented method for detecting neurodegeneration in a patient. The method includes obtaining, with at least one processor, a first diffusion magnetic resonance imaging (MRI) scan of the brain of the patient. The method also includes obtaining, with at least one processor, a plurality of diffusion MRI scans of a group of other brains. The method further includes generating, with at least one processor, a control diffusion MRI scan based on the plurality of diffusion MRI scans of the group of other brains. The method further includes determining, with at least one processor, a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement. The method further includes determining, with at least one processor, a differential by comparing the first anisotropy to the second anisotropy. The method further includes identifying, with at least one processor, at least one neurological disorder based on the differential and a location of the first neural tracks in the brain of the patient.

According to a non-limiting embodiment or aspect, provided is a system including at least one server computer including at least one processor. The at least one server computer is programmed and/or configured to obtain a first diffusion magnetic resonance imaging (MRI) scan of the brain of the patient. The at least one server computer is also programmed and/or configured to obtain a plurality of diffusion MRI scans of a group of other brains. The at least one server computer is further programmed and/or configured to generate a control diffusion MRI scan based on the plurality of diffusion MRI scans of the group of other brains. The at least one server computer is further programmed and/or configured to determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement. The at least one server computer is further programmed and/or configured to determine a differential by comparing the first anisotropy to the second anisotropy. The at least one server computer is further programmed and/or configured to identify at least one neurological disorder based on the differential and a location of the first neural tracks in the brain of the patient.

According to a non-limiting embodiment or aspect, provided is a computer program product including at least one non-transitory computer-readable medium including program instructions that, when executed by at least one processor, cause the at least one processor to obtain a first diffusion magnetic resonance imaging (MRI) scan of the brain of the patient. The program instructions also cause the at least one processor to obtain a plurality of diffusion MRI scans of a group of other brains. The program instructions further cause the at least one processor to generate a control diffusion MRI scan based on the plurality of diffusion MRI scans of the group of other brains. The program instructions further cause the at least one processor to determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement. The program instructions further cause the at least one processor to determine a differential by comparing the first anisotropy to the second anisotropy. The program instructions further cause the at least one processor to identify at least one neurological disorder based on the differential and a location of the first neural tracks in the brain of the patient.

According to a non-limiting embodiment or aspect, provided is a method of treating a neurological disorder in a patient. The method includes receiving, from a computing device including the computer program product described above, an identification of the at least one neurological disorder. The method further includes treating, based on the identification, the at least one neurological disorder.

Other non-limiting embodiments or aspects are set forth in the following numbered clauses:

Clause 1: A computer-implemented method for detecting neurodegeneration in a patient, comprising: obtaining, with at least one processor, a first diffusion magnetic resonance imaging (MRI) scan of the brain of the patient; obtaining, with at least one processor, a plurality of diffusion MRI scans of a group of other brains; generating, with at least one processor, a control diffusion MRI scan based on the plurality of diffusion MRI scans of the group of other brains; determining, with at least one processor, a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement; determining, with at least one processor, a differential by comparing the first anisotropy to the second anisotropy; and identifying, with at least one processor, at least one neurological disorder based on the differential and a location of the first neural tracks in the brain of the patient.

Clause 2: The method of clause 1, wherein the control diffusion MRI scan is generated based on an average of the plurality of diffusion MRI scans of the group of other brains.

Clause 3: The method of clause 1 or 2, wherein the first anisotropy is a measure of a segment of the first neural tracks having a length of at least 10 mm, and the second anisotropy is a measure of a segment of the second neural tracks having a length of at least 10 mm.

Clause 4: The method of any of clauses 1-3, wherein the first anisotropy is a measure of a segment of the first neural tracks having a length of at least 50 mm, and the second anisotropy is a measure of a segment of the second neural tracks having a length of at least 50 mm.

Clause 5: The method of any of clauses 1-4, wherein the differential comprises at least a 15% difference of the first anisotropy from the second anisotropy.

Clause 6: The method of any of clauses 1-5, wherein the differential comprises at least a 30% difference of the first anisotropy from the second anisotropy.

Clause 7: The method of any of clauses 1-6, wherein the first anisotropy comprises a value of spin density less than a value of spin density of the second anisotropy.

Clause 8: The method of any of clauses 1-7, wherein the location of the first neural tracks is in a cingulum region, a corpus callosum region, a corticostriatal pathway, or a corticospinal pathway of the brain of the patient, and wherein the at least one neurological disorder comprises Huntington's disease.

Clause 9: A system comprising at least one server computer including at least one processor, the at least one server computer programmed and/or configured to: obtain a first diffusion magnetic resonance imaging (MRI) scan of the brain of the patient; obtain a plurality of diffusion MRI scans of a group of other brains; generate a control diffusion MRI scan based on the plurality of diffusion MRI scans of the group of other brains; determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement; determine a differential by comparing the first anisotropy to the second anisotropy; and identify at least one neurological disorder based on the differential and a location of the first neural tracks in the brain of the patient.

Clause 10: The system of clause 9, wherein the control diffusion MRI scan is generated based on an average of the plurality of diffusion MRI scans of the group of other brains.

Clause 11: The system of clause 9 or 10, wherein the first anisotropy is a measure of a segment of the first neural tracks having a length of at least 50 mm, and the second anisotropy is a measure of a segment of the second neural tracks having a length of at least 50 mm.

Clause 12: The system of any of clauses 9-11, wherein the differential comprises at least a 30% difference of the first anisotropy from the second anisotropy.

Clause 13: The system of any of clauses 9-12, wherein the first anisotropy comprises a value of spin density less than a value of spin density of the second anisotropy.

Clause 14: The system of any of clauses 9-13, wherein the location of the first neural tracks is in a cingulum region, a corpus callosum region, a corticostriatal pathway, or a corticospinal pathway of the brain of the patient, and wherein the at least one neurological disorder comprises Huntington's disease.

Clause 15: A computer program product comprising at least one non-transitory computer-readable medium including program instructions that, when executed by at least one processor, cause the at least one processor to: obtain a first diffusion magnetic resonance imaging (MRI) scan of the brain of the patient; obtain a plurality of diffusion MRI scans of a group of other brains; generate a control diffusion MRI scan based on the plurality of diffusion MRI scans of the group of other brains; determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement; determine a differential by comparing the first anisotropy to the second anisotropy; and identify at least one neurological disorder based on the differential and a location of the first neural tracks in the brain of the patient.

Clause 16: The computer program product of clause 15, wherein the control diffusion MRI scan is generated based on an average of the plurality of diffusion MRI scans of the group of other brains.

Clause 17: The computer program product of clause 15 or 16, wherein the first anisotropy is a measure of a segment of the first neural tracks having a length of at least 50 mm, and the second anisotropy is a measure of a segment of the second neural tracks having a length of at least 50 mm.

Clause 18: The computer program product of any of clauses 15-17, wherein the differential comprises at least a 30% difference of the first anisotropy from the second anisotropy.

Clause 19: The computer program product of any of clauses 15-18, wherein the location of the first neural tracks is in a cingulum region, a corpus callosum region, a corticostriatal pathway, or a corticospinal pathway of the brain of the patient, and wherein the at least one neurological disorder comprises Huntington's disease.

Clause 20: A method of treating a neurological disorder in a patient, comprising: receiving, from a computing device comprising the computer program product of any of clauses 15-19, an identification of the at least one neurological disorder; and treating, based on the identification, the at least one neurological disorder.

Clause 21: The method of clause 20, wherein the neurological disorder is Huntington's Disease.

Clause 22: The method of clause 20 or 21, wherein the differential of the first neural tracks in the brain of the patient is measured in the cingulum, corpus callosum, corticostriatal pathway, corticospinal pathway, or whole brain of the patient.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Additional advantages and details are explained in greater detail below with reference to the non-limiting, exemplary embodiments that are illustrated in the accompanying figures, in which:

FIG. 2 provides a table of demographic information from evaluations of differential tractography according to non-limiting embodiments or aspects;

FIG. 7A provides a table of tract volume measurements in Huntington's disease (HD) subjects A through H, generated from a method for detecting neurodegeneration according to non-limiting embodiments or aspects;

FIG. 7B provides a table of tract volume measurements in Huntington's disease (HD) subjects I through P, generated from a method for detecting neurodegeneration according to non-limiting embodiments or aspects;

FIG. 9A provides a table of correlation analysis between tract volume and clinical scores in longitudinal data, generated from a method for detecting neurodegeneration according to non-limiting embodiments or aspects;

FIG. 9B provides a table of correlation analysis between tract volume and clinical scores in longitudinal data, generated from a method for detecting neurodegeneration according to non-limiting embodiments or aspects;

FIG. 10A provides a table of correlation analysis between tract volume and clinical scores in cross-sectional data, generated from a method for detecting neurodegeneration according to non-limiting embodiments or aspects;

FIG. 10B provides a table of correlation analysis between tract volume and clinical scores in cross-sectional data, generated from a method for detecting neurodegeneration according to non-limiting embodiments or aspects;

FIG. 10C provides a table of correlation analysis between tract volume and clinical scores in cross-sectional data, generated from a method for detecting neurodegeneration according to non-limiting embodiments or aspects;

FIG. 10D provides a table of correlation analysis between tract volume and clinical scores in cross-sectional data, generated from a method for detecting neurodegeneration according to non-limiting embodiments or aspects;

DETAILED DESCRIPTION

Figure 1:
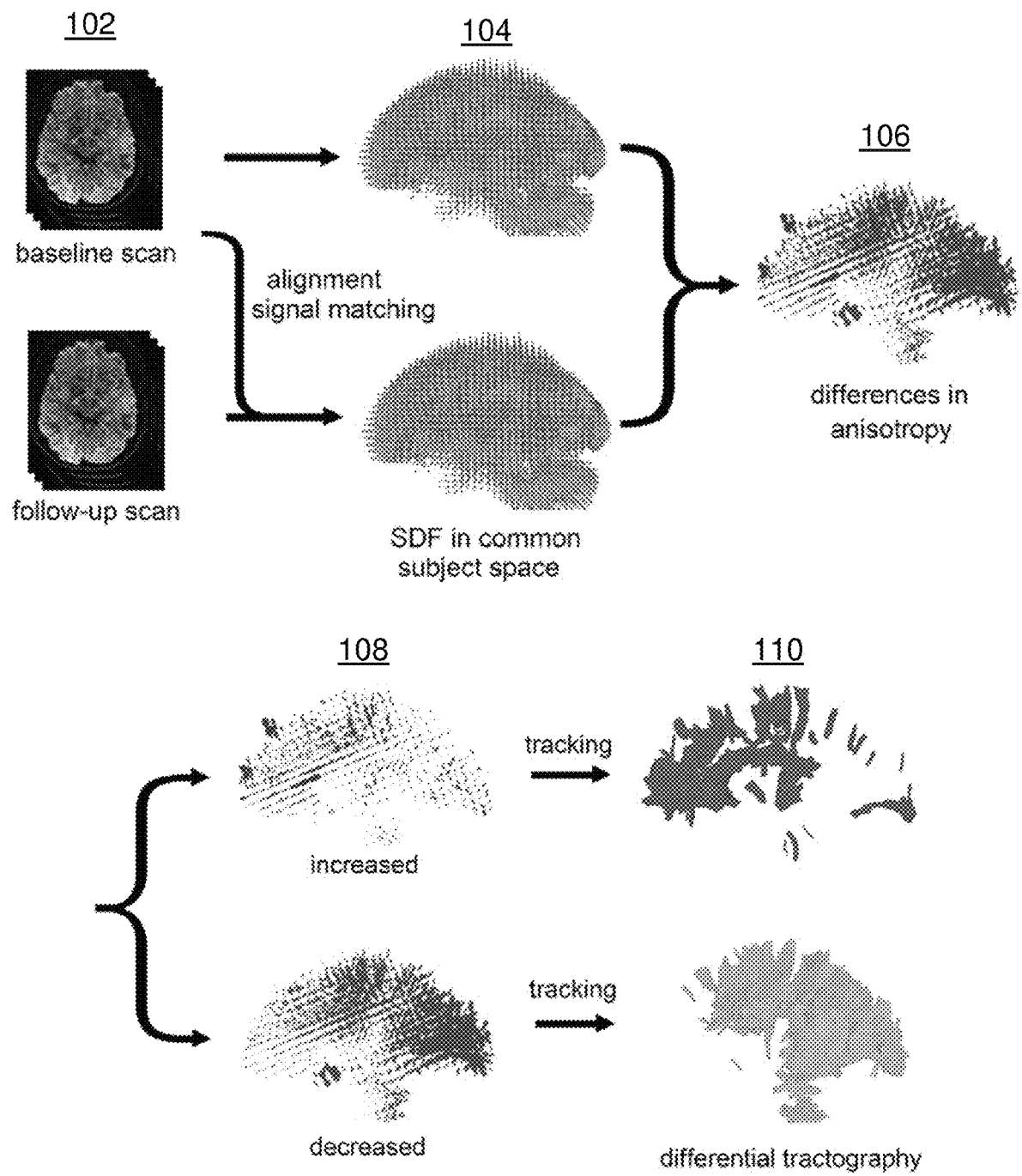
FIG. 1 provides a flow chart of differential tractography according to non-limiting embodiments or aspects.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to, human beings.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

As used herein, the term "computing device" or "computer" may refer to one or more electronic devices configured to process data. A computing device may, in some examples, include the necessary components to receive, process, and output data, such as a display, a processor, a memory, an input device, and a network interface. A computing device may be a server, a mobile device, a desktop computer, a subsystem or integrated part of a genomic sequencer or sequence analyzer, and/or the like. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices.

As used herein, "interface" refers, in the context of programming and software modules, to the languages, codes and messages that programs or modules use to communicate with each other and to the hardware, and includes computer code or other data stored on a computer-readable medium that may be executed by a processor to facilitate the interaction between software modules. In some aspects of the methods and systems described herein, software modules, such as the variant calling module, the tumor phylogeny or modules and the machine learning modules are designed as separate software components, modules, or engines, with each requiring specific data input formats, and providing specific data output formats, and, in non-limiting examples, an interface may be used to facilitate such communication between components.

As used herein, the term "graphical user interface" or "GUI" refers to a generated display with which a user may interact, either directly or indirectly (e.g., through a keyboard, mouse, touchscreen, and/or the like).

As used herein, the term "electronic health record system" refers to a system including at least one computing device and at least one database for storing records of data corresponding to one or more patients, the data being representative of one or more attributes of a respective patient. As used herein, the term "patient cohort data" refers to data representative of one or more attributes of a plurality of patients.

As used herein, the term "satisfying" with respect to a threshold may include meeting and/or exceeding a threshold, which may include meeting or having a value less than a minimum-type threshold, and meeting or having a value greater than a maximum-type threshold.

As used herein, the terms "medical treatment" or "treating," with respect to a patient, refers to taking one or more actions to optimize quality of life (e.g., palliative care) and/or improve the current and/or future condition of the patient. Medical treatment may include, but is not limited to, one or more of the following actions: administering a medication or other aid (e.g., oxygen) to the patient, modifying a level of monitoring of the patient, conducting one or more tests of the patient, conducting one or more surgical or reparative operations on the patient, providing one or more therapies or therapeutics to the patient, employing one or more medical devices for use on, in, or by the patient, modifying the position of the patient, increasing or reducing patient stimulation, modifying a diet of the patient, modifying an environment of the patient, and/or the like. As used herein, the term "neuromorbidity" may refer to a neurologic morbidity, including physical complications or problems caused by medical treatment, trauma, medical condition, or disease, such as an infection. Neuromorbidity may include, but is not limited to, cognitive decline, delirium, chronic pain, seizures, intracranial hemorrhage, stroke, impairment or loss of consciousness, seizures, ischemic stroke, intracerebral hemorrhage, cerebral edema, delirium, neuromuscular weakness, and/or the like.

Differential Tractography

Described herein is a novel method called "differential tractography" to provide a track-based biomarker of neurodegeneration. This method compares repeat scans of the same individual, or a scan of an individual to a control scan, to capture neurodegeneration reflected by a differential (e.g., decrease) of anisotropy. To achieve a higher specificity, we imbued the deterministic fiber tracking algorithm (see Yeh et al., *Generalized q-sampling imaging*, IEEE Trans. Med. Imaging, 2010, Vol. 29, p. 1626-35 (referred to herein as "Yeh 2010"), the disclosure of which is hereby incorporated by reference in its entirety) with a novel "tracking-the-difference" paradigm. The algorithm was realized by adding a criterion to track along trajectories on which a decrease of anisotropy was found between repeat scans.

With specific reference to FIG. 1, and in non-limiting embodiments or aspects, provided is a flow chart of differential tractography. In step 102, the baseline and follow-up scans of the same subject are spatially aligned, and the diffusion signals are scaled to the same unit. It will be appreciated that the baseline scan may also be that of a control scan and the follow-up scan may that be of a patient scan. In step 104, the spin distribution function (SDF) from the two scans are reconstructed in the same common subject space. In step 106, the difference in the anisotropic component of SDF is computed for each fiber orientation. In step 108, increased and decreased anisotropy values are separated to guide a "tracking-the-difference" algorithm. In step 110, differential tractography shows the exact segment of tracks with increased and decreased anisotropy, respectively. The tracks with decreased anisotropy may suggest possible neuronal injury. The tracks with increased anisotropy may be used to estimate the number of false findings.

Integrating this "tracking-the-difference" paradigm into the fiber tracking process results in a new tractography modality that tracks the exact portion of pathways exhibiting substantial differences in anisotropy. The additional criterion ignores unaffected regions and enhances meaningful findings related to neuronal injury. To implement differential tractography, we may use one anisotropy value for each fiber population to calculate its longitudinal change. The fractional anisotropy (FA) derived from DTI is a voxel-based measurement, and thus all fiber orientations within the same voxel will inherit the same anisotropy value. As used herein, "voxel" may refer to a unit of graphic information that defines a point in three-dimensional space; compare to "pixel," referring to a point in two-dimensional space. To overcome this limitation, we use the anisotropic component of the SDF (see Yeh 2010) as an anisotropy measurement for each fiber population. SDF provides one anisotropy measurement for each fiber population. This approach is more robust against partial volume effect and achieves high accuracy. To further maximize the detection power, we used a diffusion MRI acquisition that sampled 22 diffusion sensitizations (b-values) at 257 directions, a substantial improvement. The higher number of diffusion sensitizations significantly increased the chance to detect neuronal injury that involves only a subtle change in the restricted diffusion.

With specific reference to FIG. 2, depicted is a table of demographic information from evaluations of differential tractography. To evaluate the performance, we applied differential tractography to patients with four different clinical scenarios at different stages of neuronal injury. The first scenario was multiple sclerosis (MS), with the first episode of optic neuritis. The baseline scans were acquired right after the onset of the visual symptom, and the follow-up diffusion MRI scans were acquired six months after. This scenario tested differential tractography at the early stage of neuronal injury to explore its sensitivity, and any meaningful findings may be located near the visual pathways. The second scenario was the manifested Huntington's disease (HD) with worsening clinical motor scores during the interval of their repeat MRI scans. We examined whether differential tractography could detect progressing neuronal injury at striatal pathways that are commonly affected by the disease.

The third scenario studied the neuronal injury in an amyotrophic lateral sclerosis (ALS) patient with a deteriorating functional motor score. We examined whether differential tractography could be correlated with the patient's clinical presentation. In the fourth scenario, we applied differential tractography to an epileptic patient treated by anterior temporal lobectomy. The baseline scan was acquired before the surgery, and the follow-up scan was acquired one year after the surgery. Using longitudinal scans, we examined whether differential tractography could correctly locate pathways with established neuronal injury after surgery, and meaningful findings may be in pathways previously connected to the area of resection. We also applied differential tractography to a healthy subject to demonstrate how differential tractography may capture false results.

MRI Experiments on Clinical Patients with Neurological Disorders

The diffusion MRI acquisition included a baseline scan and another follow-up scan (acquired months later) of the same subject. We acquired scans on six patients with different neurological diseases, including MS, HD, ALS, and epilepsy, in addition to one healthy volunteer. The diffusion data were acquired on a 3T Tim Trio System (Siemens, Erlangen, Germany) using a pulsed-gradient spin-echo 2D echo-planar imaging sequence. A 32-channel coil was used with a head stabilizer to limit head motion. Each diffusion MRI scan acquired 22 b-values ranging from 0 to 7000 s/mm$^2$ at a total of 257 diffusion sampling directions using a q-space imaging scheme. The in-plane resolution and slice thickness were 2.4 mm. Echo time (TE)=154 ms, and repetition time (TR)=9500 ms. The total scanning time was 45 min. The same protocol using a multi-band sequence may have a shorter scanning time (e.g., 12 min.).

Empirical Distribution of Water Diffusion

The empirical distribution of water diffusion may be calculated from diffusion-weighted signals using generalized q-sampling imaging (GQI). This empirical distribution has no assumption of the underlying distribution (e.g., Gaussian distribution), and thus it can be applied to a variety of fiber or biological conditions. The empirical distribution calculated from GQI, termed the spin distribution function (SDF), has a different physical definition from the diffusivity calculated from DTI that quantifies how fast the diffusion is. SDF quantifies the accumulated spin density of restricted diffusion sampled at any orientations, and SDF can be calculated using the following formula:

$$\Psi_0(r, \hat{u}) = Z_0 \sum_i W_0(r, i) \text{sinc}\left(\sigma\sqrt{6Db(i)}\,\hat{g}(i), \hat{u}\right) \quad \text{Formula 1}$$

where $\Psi(r,\hat{u})$ is the SDF value oriented at $\hat{u}$ and sampled from a voxel located at r. $Z_0$ is a scaling constant to convert the arbitrary unit of the diffusion signals to a density unit, and i iterates through each diffusion-weighted signals $W(r,i)$, where $b(i)$ is the b-value, and $\hat{g}(i)$ is the direction of the diffusion sensitization gradient. $\sigma$ is the diffusion sampling ratio controlling the displacement range of the diffusing spins (e.g., 1.25). D is the diffusivity of free water.

We then calculated the SDFs of the follow-up scan and transformed them into the space of the baseline scan (see FIG. 1) so that they could be directly compared. The transformation was done using q-space diffeomorphic reconstruction (QSDR), a method that generalized GQI to accept spatial transformation in the reconstruction. QSDR allowed us to simultaneously reconstruct and transform SDF from the follow-up scan to the space of the baseline scan using the following formula:

$$\Psi_1(r, \hat{u}) = Z_1 \sum_i W_1(\varphi(r), i) \text{sinc}\left(\sigma\sqrt{6Db(i)}\,\hat{g}(i), J(r)\hat{u}\right) \quad \text{Formula 2}$$

where $\Psi(r)$ transforms spatial coordinate r from the space of the baseline scan to that of the follow-up scan. $W_1(\Psi(r),i)$ is the diffusion-weighted signals at coordinate $\Psi(r)$. $J(r)$ is the Jacobian matrix at the same coordinate that rotates the unit vector $\hat{u}$. The other variables follow the same notations in Formula 1.

For scans of the same subject, it may be assumed that there is only rigid body transformation (e.g., only rotation or translocation) between scans, in which the transformation is a matrix-vector multiplication. This assumption may be violated if there is a massive tissue distortion due to edema or tissue removal, and a nonlinear spatial registration may be used in QSDR to handle the problem. The rigid body transformation matrix may be obtained by linear registering the $b_0$ images (or the sum of all diffusion-weighted images). The negative of the correlation coefficient between the images from the baseline and the follow-up scans may be used as a cost function to calculate the transformation matrix. The cost function may be minimized using a gradient descent method. The rotation matrix of the rigid body transformation may be used as the Jacobian matrix for Formula 2.

It will be appreciated that the SDFs calculated from Formula 1 and Formula 2 have arbitrary units. Therefore, the $Z_1$ constant in Formula 2 may be scaled to match the same unit of $Z_0$ of in Formula 1. Signal matching may be completed using the sum of all diffusion-weighted images from two scans, according to the following formula:

$$Z_1 = Z_0 \frac{\sum_r W_1(\varphi(r), 0)}{\sum_r W_0(r, 0)} \quad \text{Formula 3}$$

The isotropic component of an SDF may then be removed by subtracting its minimum values.

To minimize the effect of free water diffusion, Formula 4 and Formula 5 may be used to provide the anisotropic component of SDF:

$$\Psi'_0(r, \hat{u}) = \Psi_0(r, \hat{u}) - \min_{\hat{u}} \Psi_0(r, \hat{u}) \quad \text{Formula 4}$$

$$\Psi'_1(r, \hat{u}) = \Psi_1(r, \hat{u}) - \min_{\hat{u}} \Psi_1(r, \hat{u}) \quad \text{Formula 5}$$

It is noteworthy that this anisotropy measurement has a different physical meaning from the fractional anisotropy (FA) calculated in DTI. FA is a ratio between zero and one calculated from diffusivities and has no unit. The anisotropic SDF has the same physical unit of the SDF, which is the spin density of diffusing water.

Tracking Differences in the SDF

To track differences along the existing fiber pathways, we first determined the local fiber orientations using the peaks on the sum of $\Psi_0(r,\hat{u})$ and $\Psi_1(r,\hat{u})$, and then the anisotropy estimated from the summed SDF was used to filter out noisy fibers and to define the termination of the white matter tracks. The percentage difference in the anisotropy between baseline and follow-up scans may then be calculated according to the following formula:

$$\Psi_d(r, \hat{u}) = \frac{2(\Psi'_1(r, \hat{u}) - \Psi'_0(r, \hat{u}))}{\Psi'_1(r, \hat{u}) + \Psi'_0(r, \hat{u})} \times 100\% \quad \text{Formula 6}$$

The percentage changes in the anisotropy, $\Psi_d(r,\hat{u})$, can have positive values (see blue SDFs in FIG. 1), which indicates an increase in the density of anisotropic diffusion, or negative values (see red SDFs in FIG. 1), which indicates a decrease in the density of anisotropic diffusion.

An additional tracking-the-differences criterion was added to the fiber tracking algorithm to track the exact segment with a decrease or an increase in the anisotropy larger than a change threshold. For example, to track pathways with an increase of anisotropy, the additional criterion checked whether the increase of anisotropy was higher than a predefined value of percentage change (e.g., 20%), and continued tracking as long as the criterion was satisfied, according to the following formula:

$$\Psi_d(r,\hat{a}) > \theta^+ \quad \text{Formula 7}$$

where $\hat{a}$ is the local fiber directions used in the fiber tracking algorithm. Similarly, to track pathways with decreased anisotropy, the criterion continued tracking if the decrease of anisotropy was lower than a predefined value of percentage change (e.g., −20%), according to the following formula:

$$\Psi_d(r,\hat{a}) < \theta^- \quad \text{Formula 8}$$

The criteria of Formula 7 and Formula 8 allowed us to track two different sets of pathways, one for increased anisotropy and one for decreased anisotropy. The other existing criteria (e.g., seeding strategy, propagation interval, angular threshold, length constraint, etc.) may remain in effect. It will be appreciated that the angular and anisotropy thresholds in the tracking algorithm were still used in differential tractography to eliminate noisy fiber and to ensure a correct white matter coverage. Formula 7 and Formula 8 may be referred to as a positive change threshold and a negative change threshold, respectively, and may serve as additional constraints to limit the findings to the exact segment of pathways with a substantial change in the anisotropy value.

In one non-limiting embodiment, the differential tractogram may be obtained by placing a plurality of seeding points (e.g., 5,000,000) in the white matter. The angular threshold may be randomly selected (e.g., between 15° and 90°). The step size may be 1 mm, and the anisotropy threshold may be automatically determined using diffusion spectrum magnetic resonance imaging (DSI) software. One or more iterations of topology-informed pruning may be applied to the tractography to remove noisy findings. Differential tractography may be applied with different change thresholds (e.g., 5%, 10%, 15%, . . . ,50%, etc.) and length thresholds (e.g., 5 mm, 10 mm, 15 mm, . . . , 50 mm, etc.). Tracks with lengths shorter than the length threshold may be discarded, and the results of different length threshold and change threshold may be compared to determine the effect on the sensitivity and specificity of differential tractography.

Neuronal Injury Reflected by a Decrease of Anisotropy

Figure 3:
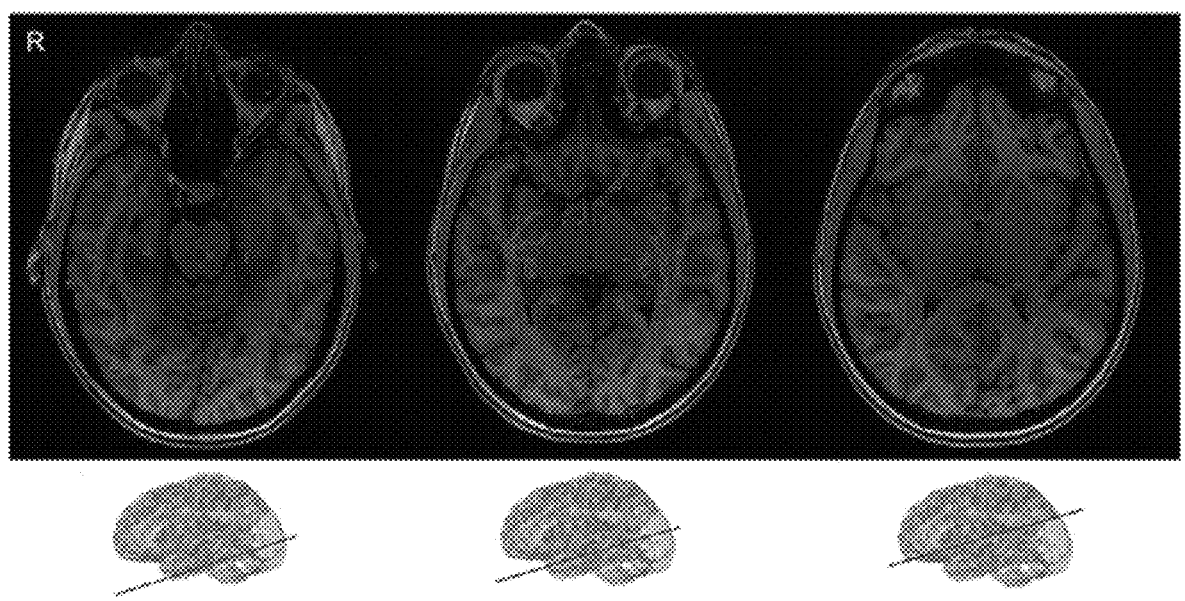
FIG. 3 provides scan data from intermediate results of differential tractography according to non-limiting embodiments or aspects.

With specific reference to FIG. 3, and in non-limiting embodiments or aspects, depicted are the intermediate results of differential tractography applied to an MS patient with optic neuritis (patient #1 shown in FIG. 2). The baseline scan was acquired right after the onset, whereas the follow-up scan was acquired six months after. For each fiber orientation in a voxel, differential tractography compares the anisotropy differences between two MRI scans in a common subject space. The fiber orientations with a decrease of anisotropy larger than 30% were plotted by red sticks. As shown in FIG. 3, most of the differences are distributed throughout the entire white matter regions. This may be due to local signal variations or registration error.

Figure 4:
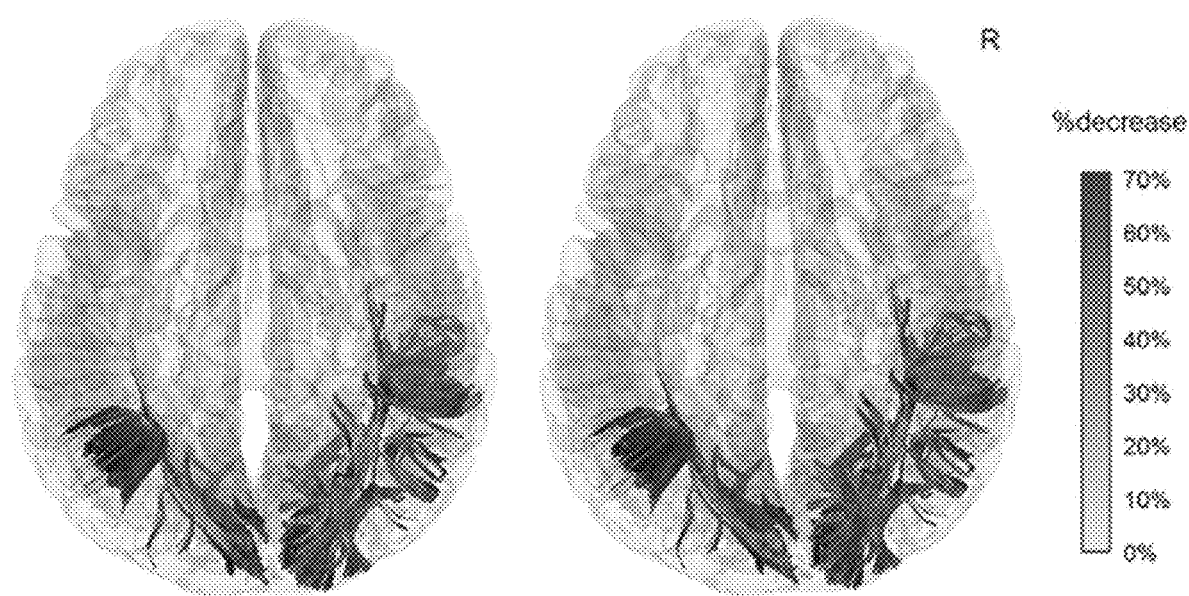
FIG. 4 provides processed scans using differential tractography where identified neural tracks are connected into continuous trajectories, according to non-limiting embodiments or aspects.

With specific reference to FIG. 4, an in non-limiting embodiments or aspects, depicted are processed scans where identified neural tracks are connected into continuous trajectories. To eliminate spurious local differences, we applied the "tracking-the-difference" algorithm to the track and linked all local differences together into continuous trajectories. The short fragments may be discarded using a length threshold (e.g., 40 mm). The use of a length threshold makes use of the observation that local random error does not propagate along fiber pathways, whereas true findings due to neuronal injury will form a continuous decrease of anisotropy along the fiber bundles. A length threshold may effectively differentiate between local random error and neuronal injury to eliminate false results.

As shown in FIG. 4, the resulting 3D presentation is the differential tractogram of the patient showing the exact segment of pathways with a substantial decrease in anisotropy. The tractography may be rendered by directional colors (shown in FIG. 4, left) or severity-coded color (shown in FIG. 4, right) to provide information about the spatial location. Directional colors are rendered as red (left-right), green (anterior-posterior), and blue (superior-inferior), whereas severity-coded colors are provided according to severity of neural injury (e.g., yellow: 0%, red: 70% decrease). The severity of the axonal damage may be quantified by percentage decrease of anisotropic diffusion. As shown in FIG. 4, the differential tractogram reveals a heterogeneous decrease of anisotropy between 20% and 50%. These findings are in the bilateral primary visual pathways or their collateral connections. The location of the finding matches well with the patient's medical history of visual loss in both left and right quadrants. The topology of affected pathways may present a ripple effect, where not only the primary visual pathway is affected, but also connections to the visual cortex may show a decrease in anisotropy. Although the patient was fully recovered from symptoms during the follow-up scan, differential tractography still captures subclinical change near the bilateral optic radiation.

Differential Tractography on Patients with Neurological Diseases

Figure 5A:
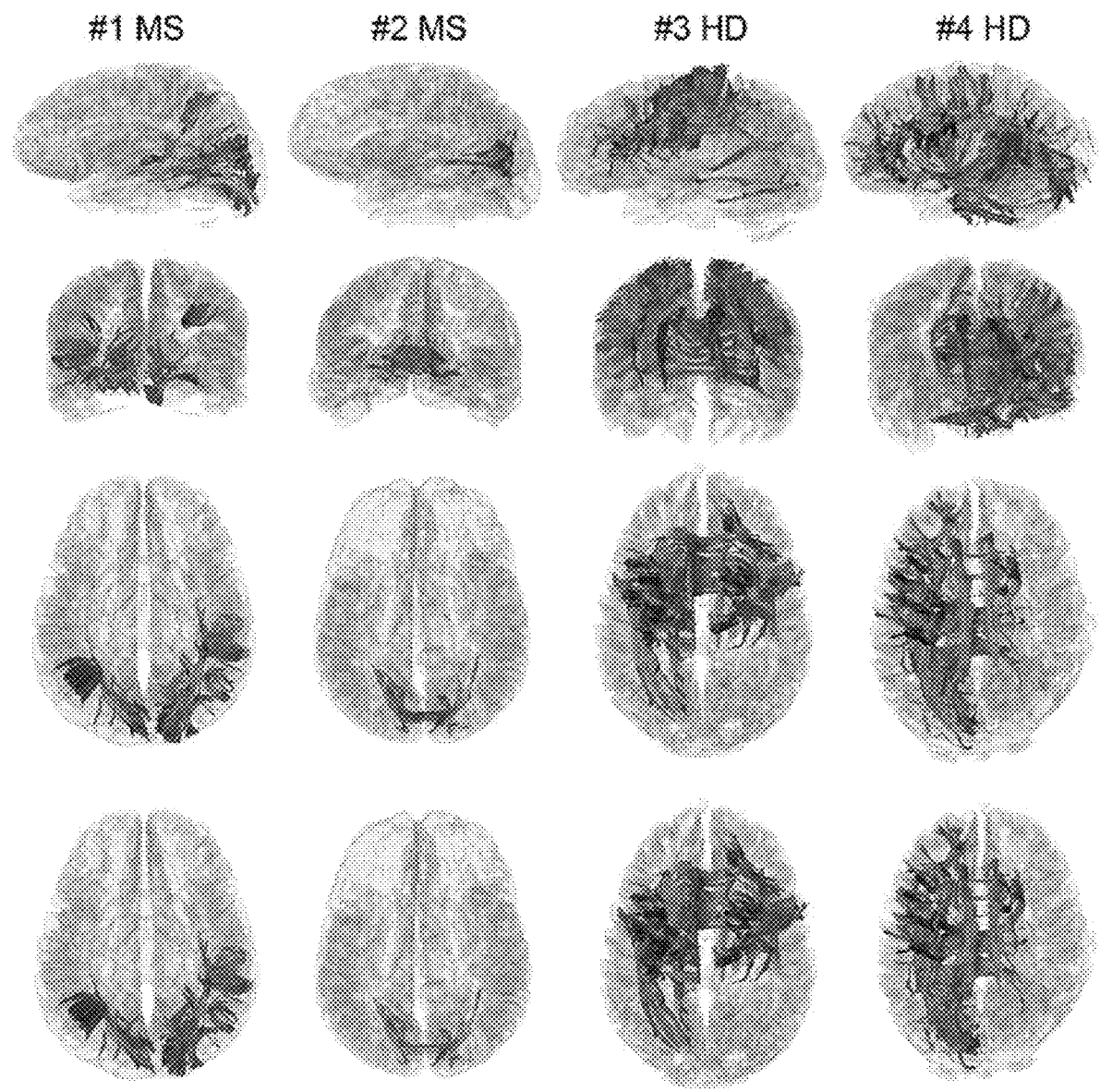
FIG. 5A provides scan data of differential tractography applied to patients with different neurological disorders, according to non-limiting embodiments or aspects.
Figure 5B:
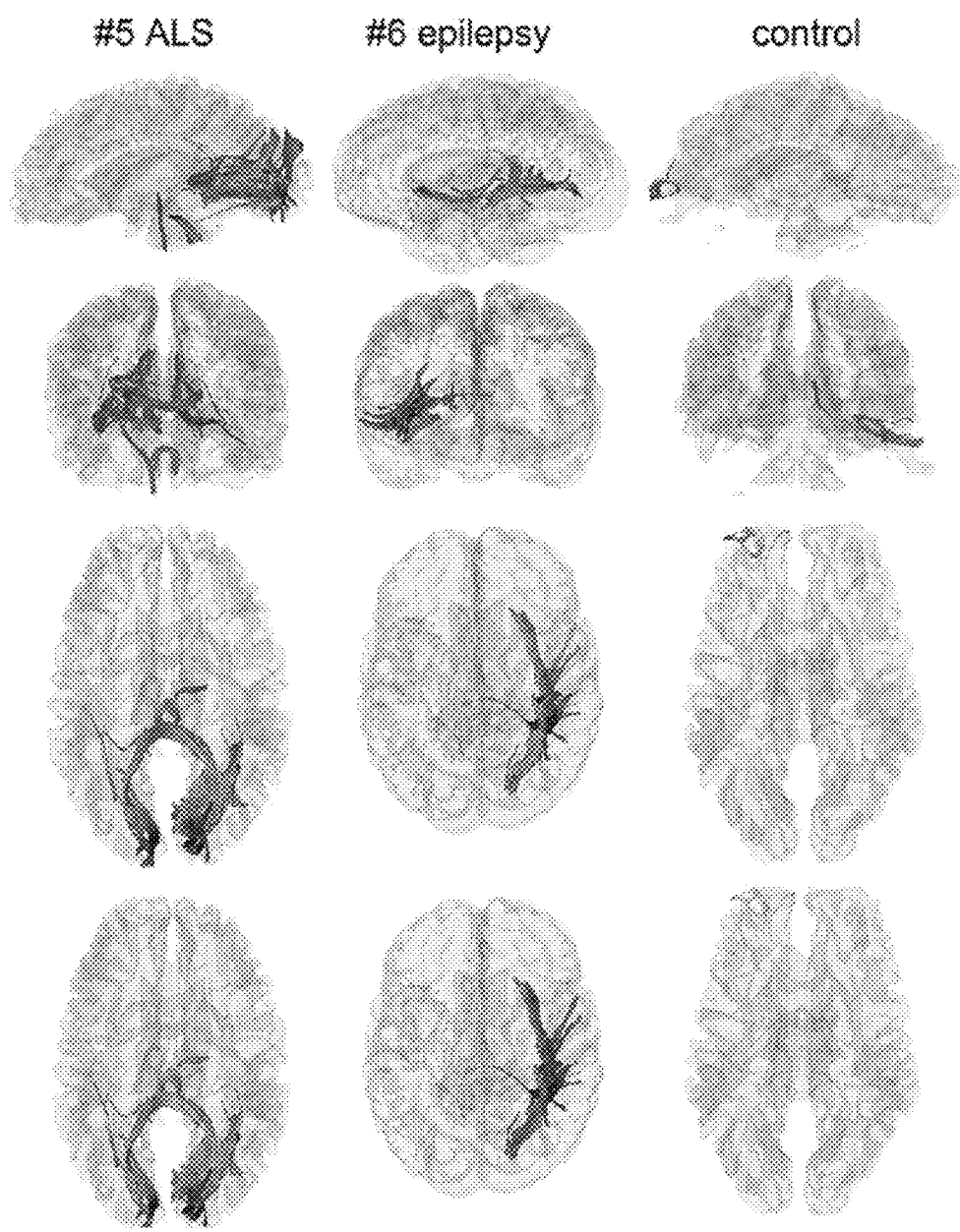
FIG. 5B provides scan data of differential tractography applied to patients with different neurological disorders, including a control patient, according to non-limiting embodiments or aspects.

With specific reference to FIGS. 5A and 5B, and in non-limiting embodiments or aspects, provided is the application of differential tractography to patients with different neurological disorders. The scan subjects include patients with MS (patients #1 and #2), HD (patients #3 and #4), ALS (patient #5), and epilepsy (patient #6) (see FIG. 2 for patient information). The first three rows show the differential tractograms in three views (left sagittal from left, coronal from front, and axial from top) using directional colors, where the last row shows the differential tractogram with yellow-red colors representing the percentage decrease of anisotropy.

With specific reference to FIG. 5A, the first notable finding comparing MS patients #1 and #2 is that the volume of affected pathways and their decrease of anisotropy reflect the severity of their clinical symptoms. The medical history of patient #1 indicated a more severe drop in visual acuity to 20/400 in addition to visual field defect in all quadrants, while patient #2 only had a decrease of visual acuity to 20/125 with only superior altitudinal visual field defect. The higher severity in patient #1 is reflected by a larger volume of affected pathways diffusion (patient #1: 55681.6 mm$^3$, patient #2: 26124 mm$^3$) and a larger decrease of anisotropy shown in the last row. This indicates that differential tractography may be used to evaluate disease severity using either the volume of affected tracks or the decrease of their anisotropy.

With specific reference to FIG. 5A, the differential tractogram of HD patients #3 and #4 in FIG. 5A both shows affected pathways around the stratum. The finding matches well with the understanding that striatal pathways are usually involved in Huntington's disease. Moreover, the differential tractogram in patient #4 has a broader involvement extending to brainstem and cerebellum, suggesting a worse motor performance. This finding comported with the patient's medical history of a higher motor score of 64. The patient also had more asymmetric dystonia, matching the asymmetry presentation of the differential tractography.

With specific reference to FIG. 5B, patient #5 is an ALS patient. It is noteworthy that this patient had mostly lower motor neuron symptoms (e.g., weakness), and thus might not have positive findings in the brain. The differential tractogram of this patient was obtained using a 15% change threshold, because the 30% change threshold yielded no findings. Differential tractography reveals a minor decrease in this patient, where other cases depicted in FIGS. 5A and 5B have mostly larger than 30% decrease. This may further be explained by the fact that the patient had predominantly lower motor neuron symptoms affecting predominately peripheral nerves. Therefore, the findings in the central nervous system may be only subclinical. Nonetheless, when the change threshold was lowered to 15%, differential tractography showed affected pathways in the right lower corticospinal pathway (blue-purple colored), superior cerebellar peduncle, and posterior corpus callosum, as shown in FIG. 5B. The right corticospinal pathway involvement corroborated the patient's history of left side involvement.

With specific reference to FIG. 5B, patient #6 was a 51-year-old male with a right anterior lobectomy. He was previously an epileptic patient with recurrent epilepsy. The MRI scans were done before the surgery and one year after the surgery. Differential tractography accurately locates the location of the surgical resection in the mesial structures and approximately 5 cm of the anterior temporal neocortex. Moreover, it further reveals the pathways that were affected by the resection. While the surgical resection only removed part of the temporal gyri, the affected pathways involve much more extended connection networks. Furthermore, the last row shows that the decrease of anisotropy is mostly higher than 50%, indicating a considerable axonal loss due to the surgical removal of the brain tissue.

With specific reference to FIG. 5B, the last column shows the differential tractogram of a control. We applied the same settings to examine how differential tractography may capture false results. The result shows a mild decrease of anisotropy as presented by yellow tracks in the last row, a clue that the change may be a false positive result. Furthermore, there are only 74 findings located at the prefrontal cortex, and these findings are relatively insignificant compared to those of the patient population that shows thousands of findings. Moreover, the location of the findings is known to be profoundly affected by the phase distortion artifact, and the findings could be due to the different level of distortion between repeat scans.

With reference to FIGS. 5A and 5B, the depicted findings provide for the quick differentiation of possible locations of neuronal injury, and for the evaluation of severity. The affected pathways in MS, HD, and ALS patients show distinctly different topology, allowing for differential diagnosis or prognosis evaluation.

Specific Application to Detection of Huntington's Disease

Huntington's disease (HD) is a neurodegenerative disorder characterized by a triad of motor, psychiatric, and cognitive symptoms. Due to its diverse manifestations, the HD scientific community has long recognized the need for a sensitive, objective and dynamic disease assessment tool. The absence of a reliable biomarker has hampered the ability to effectively conduct successful clinical trials in HD. We examined the feasibility of differential tractography as a biomarker to evaluate a correlation, at the individual level, of symptom severity and of HD progression. Differential tractography was used to map neuronal pathways with axonal injury characterized by a differential (e.g., decrease) of anisotropic diffusion pattern. We recruited sixteen patients scanned at different time points by diffusion MRI scans for differential tractography assessment and then correlated the volumetric findings with the Unified Huntington's Disease Rating Scale (UHDRS). Our results show that the volume of affected pathways revealed by differential tractography significantly correlated with the UHDRS scores, and chronological changes in differential tractography also correlated with the changes in the UHDRS with moderate correlation (r=0.5~0.6). Our results provide support that differential tractography can be used as a dynamic imaging biomarker to assess in a non-invasive manner disease progression in HD.

Huntington's disease (HD) is a progressive chronic neurodegenerative disorder, resulting from a mutation in the huntingtin gene consisting of an expansion of cytosine-adenine-guanine (CAG) repeat. The resulting protein has an expanded glutamine repeat near the N-terminus, resulting in a toxic gain of function. No effective treatment is available for HD, and the disease is universally fatal. The hallmarks of HD include choreic movements, which are the manifestation of extrapyramidal motor abnormalities and cognitive impairment. HD patients may also present with behavioral abnormalities, including, but not limited to, anxiety, depression, and compulsive behaviors. Due to the diversity of clinical symptoms, a reliable approach to evaluate disease severity and progression has been challenging in HD. The assessment of the severity of clinical symptoms relies mostly on the Unified Huntington's Disease Rating Scale (UHDRS) for disease stage stratification. UHDRS evaluates the motor, cognitive, behavioral, and functional capacity of a patient, which allows for a quantitative assessment based on the clinical presentation. Despite the usefulness of UHDRS, there is still an ongoing need for an objective imaging biomarker to assess disease onset, progression, and severity.

Structural MRI, such as T1-weighted images, may be used to quantify gross structural findings of HD patients. For clinical application, structural MRI may not be a sensitive biomarker due to large individual differences in the structural MRI. On the other hand, diffusion MRI has clinical value for HD as the microstructural change in axons can be detected by diffusion signals. The diffusion signals can be modeled by a diffusion tensor as diffusion tensor imaging (DTI) to reveal changes in both premanifest and manifest HD patients. Although DTI demonstrates a difference in HD patients at a group level, its clinical application may be limited due to its inability to resolve complex fiber orientations in the presence of free water (e.g., CSF volume). Free water acting as an artifact prevents DTI from resolving crossing fibers.

Advanced diffusion MRI may make use of multiple diffusion sensitization and hundreds of diffusion sampling directions to replace conventional DTI acquisition. This advanced acquisition approach allows for resolving complex fiber orientation by using a more sophisticated diffusion model, or by resorting to a model-free, nonparametric approach. This led to the development of beyond-DTI tractography that can handle crossing-fibers and cope with the partial volume of free water. However, beyond-DTI tractography may not be sensitive during the early neuronal degenerating stage because differences in tractography can only be demonstrated if anisotropy drops substantially below the tracking threshold. This limitation may be addressed by differential tractography, a tractography modality that focuses on the differences in anisotropy to track only the segment of the pathway with neuronal degeneration. Differential tractography may be used to compare the same subjects over two longitudinal scans, or may be used to compare one patient's scan with a cohort of control subjects. The volume of specific pathways with a differential (e.g., decrease) in anisotropy may be used as a quantitative biomarker to correlate with clinical scores. This modification allows for the derivation of a numeric value of altered pathways for each MRI scan acquired from HD patients.

Patient Characteristics and Demographics

We recruited sixteen patients, including twelve manifest HD patients and four pre-manifest patients (see Table 1, below). Manifest were symptomatic and pre-manifest were asymptomatic (all confirmed gene positive). Patients were scanned at 0, 6 and 12 months to evaluate progression. Patients had 3 scans over a period of 2 years. 12 patients had 3 scans, 1 patient had 2 scans, and 3 patients had 1 scan. The average scan interval from the first to the second scan was 6±0.39 months (range from 5 to 10 months) and the average scan interval from the first to the third scan was 12±1.01 months (range from 11 to 24 months). Patients underwent a comprehensive clinical evaluation on the day of the scan, conducted by a neurologist specializing in movement disorders. Previous to each MRI, subjects were evaluated to assess their Unified Huntington Disease Rating Scale (UHDRS) scores, including motor, behavior, cognitive and functional assessments.

TABLE 1

| | average (minimum~maximum) |
|---|---|
| Age | 50.8 (36~62) |
| Age of onset | 47 (37~56) |
| CAG Repeats | 43 (41~46) |

MRI Acquisition

Diffusion spectrum imaging data were acquired on a 3T Tim Trio System (Siemens, Erlangen, Germany) using a 32-channel coil. A head stabilizer was utilized to prevent head motion. A 25 minutes, 257-direction DSI scan with a twice-refocused spin-echo planar imaging sequence and multiple b values (repetition time=9916 ms, echo time=157 ms, voxel size=2.4 mm×2.4 mm×2.4 mm, field of view=231 mm×231 mm, maximum b-value=7000 s/mm$^2$) was performed. For anatomical comparison, we also included a high-resolution anatomical image using a 9-min T1-weighted axial MPRAGE sequence (repetition time=2110 ms, echo time=2.63 ms, flip angle=8°, number of slices=176, field of view=256 mm×256 mm, voxel size=035 mm×0.5 mm×1.0 mm).

Differential Tractography for Individuals

Figure 6:
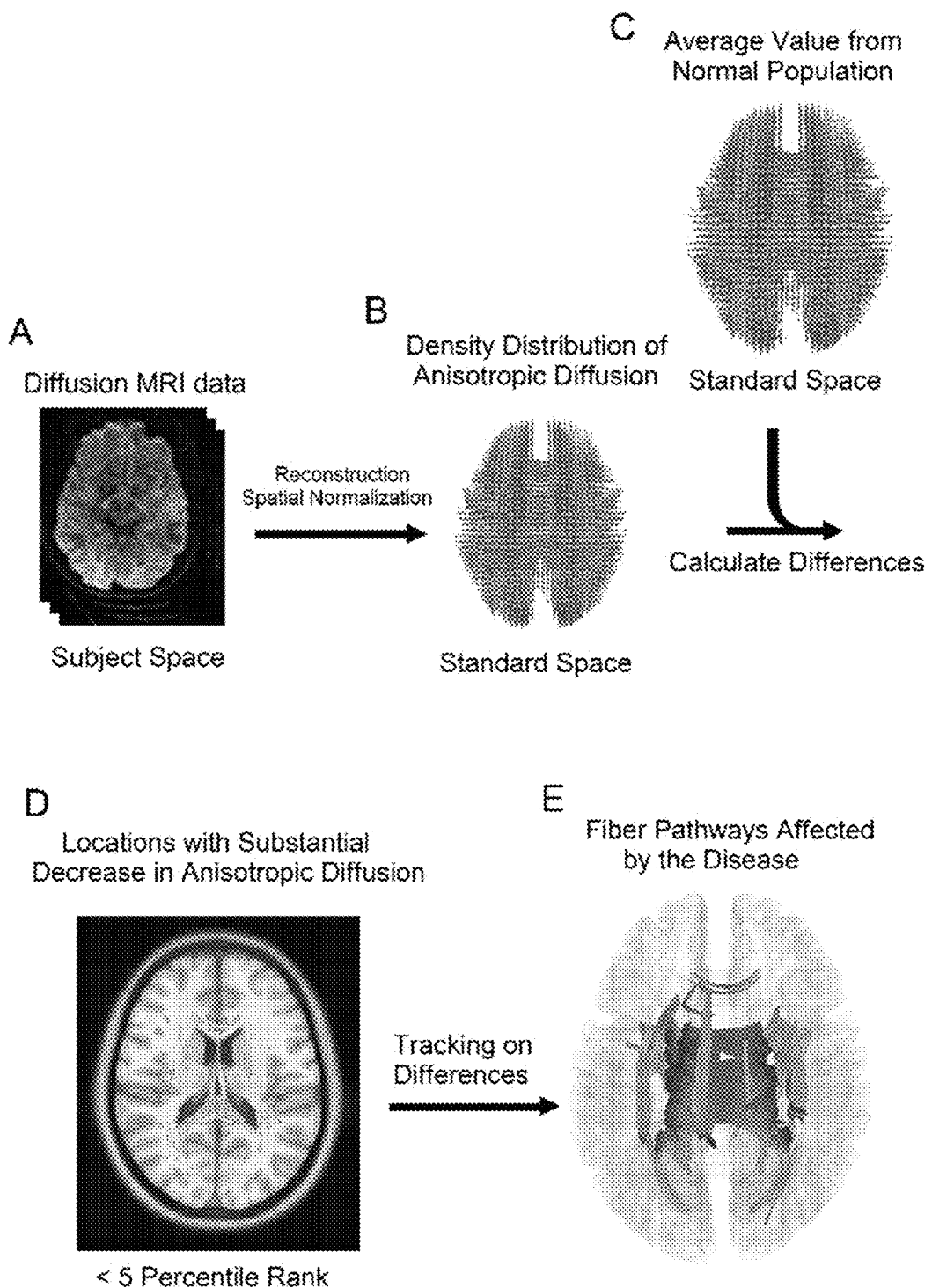
FIG. 6 provides a flow chart of a method of differential tractography analysis for use in a method for detecting neurodegeneration according to non-limiting embodiments or aspects.

The flow chart of our revised differential tractography analysis is demonstrated in FIG. 6. Diffusion imaging data of each patient (step A) was reconstructed to a common stereotaxic space using q-space diffeomorphic reconstruction (QSDR), which is a method that satisfies the conservation of diffusible spins and reconstructs diffusion MRI data in a common standard space. QSDR was applied to generate the density distribution of anisotropic diffusion (step B) for the study subject. As shown in FIG. 6, the exemplary red-green-blue color represents the orientation of diffusion, where red is left-right, green is anterior-posterior, and blue is superior-inferior. QSDR allowed us to calculate the differences in anisotropic diffusion by comparing a scan with a normal population database (CMU-60 database, step C) to show the locations of local fibers with a substantial decrease of anisotropic diffusion in study subjects, indicating changes in fiber integrity. We used a percentile rank lower than 5 of the decrease in anisotropy as the threshold to filter the results. As shown in step D, the piecewise fibers may be color-coded by orientation to indicate substantial differentials (e.g., decreases), which were then connected to guide the fiber tracking algorithm to map the exact segment of fiber bundles that were affected by the disease (step E). The tracking begins from each local fiber orientation as seeds and propagates until no orientation is found in the propagation direction. A maximum turning angle of 60° was used with a step size of 1 mm. The determined trajectories, as referred to as the "affected tracts", may be used to identify pathways with decreased connectivity.

Statistical Methods

We conducted a statistical analysis to determine the correlation of the UHDRS scores with quantitative data of each region of interest obtained by differential tractography. Data was first evaluated using a two-sided t-test which yielded a highly skewed data with wrong directionality. Logarithmic transformation to a one-sided t-test allowed data to be less skewed, correction of directionality, and better evaluation and understanding of statistical significance. Data was then organized by longitudinal and cross-sectional analyses, to determine the efficacy of the monitoring biomarker tested and have more control over brain regions tested and their correlation with clinical scores.

Repeat measures of subjects were modeled using the generalized estimating equation (GEE) model, a linear model similar to the mixed effect model that can investigate the correlation between track volume and the clinical scores that evaluated the cognitive levels and severity of the disease. Using the GEE model, we studied the correlation between differential tractography findings and UHDRS total scores for motor, cognitive, behavior, and functional capacity. Since the motor scores include assessments to evaluate the motor dysfunction in detail, we further correlated differential tractography with subscores under the motor assessment, including Total Motor Score (TMS), Dystonia Total, Chorea Total, and Rapid Alternating Movements (RAM), to see whether there were meaningful findings specific to these subscores. The same setting was also applied to the cognitive component represented by the subscore Stroop Color-Word. Lastly, the UHDRS Behavioral Total, and TFC (Total Functional Capacity) scores were correlated. On the other hand, in addition to correlating with differential tractography in the entire cerebrum, we further segmented results into five different white matter regions, including cingulum, corpus callosum, corticostriatal pathway, corticospinal pathway, and the whole brain. This allowed us to study the region-specific correlation.

Targeted fiber tracking analysis was performed for each scan using corresponding differential tractography results. Quantitative data, e.g., tract volume, for each segmented region was registered as a reference for tract involvement, such as where higher volumes indicate greater magnitude of affected tracts.

Overall, a total of 35 hypotheses were considered and each one was tested in repeat scans of pre-manifest and manifest subjects using the GEE model. We also studied these 35 correlation hypotheses for each scan time point (scans 1, 2, and 3) as three independent cross-sectional studies using the Spearman correlation model, a nonparametric method to investigate the correlation using the rank of the tract values. The longitudinal change in tract volume and the clinical scores of the above-mentioned 35 correlation hypotheses were also studied using the GEE model for the manifest patients. Moreover, three separate Spearman correlation analyses were conducted to study the change between scan 1 and 2, scan 1 and 3, and scan 2 and 3. Each hypothesis was tested initially using a two-tailed t-test, and posteriorly converted to a one-sided tail t-test. A p-value of 0.05 or less was considered statistically significant. All the analyses were conducted in SAS 9.3. The statistics of this study and its interpretation were supervised by a statistician.

Individual Differential Tractography Results

FIGS. 7A and 7B depict differential tractography measurements in all HD subjects. Affected fiber pathways in all manifest and premanifest subjects were mapped automatically by differential tractography analysis. The UHDRS Total Motor Score (TMS) and differential tractography results were assessed independently. Differential tractography progression was demonstrated in 9 manifest subjects (75%), and in 1 premanifest subject (25%) with a time-dependent increased volume of affected tracts.

Figure 8A:
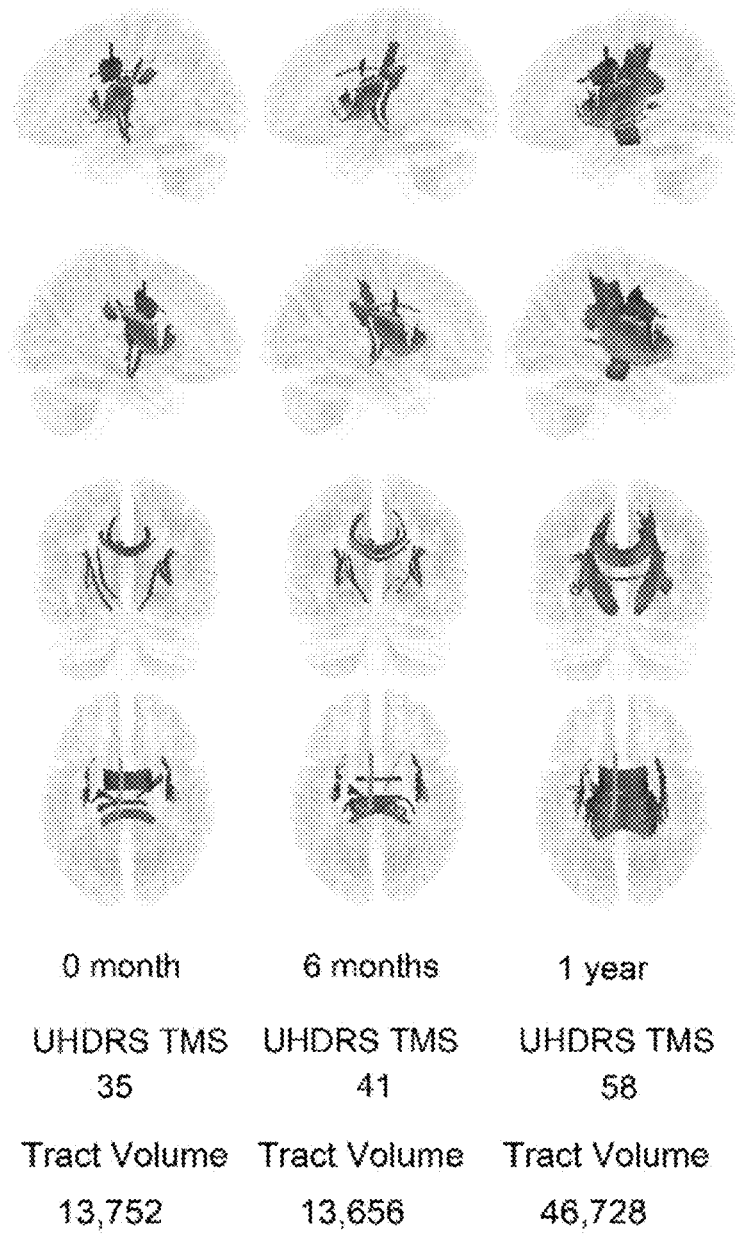
FIG. 8A provides scan and measurement data mapped by differential tractography for subject A, according to non-limiting embodiments or aspects.
Figure 8B:
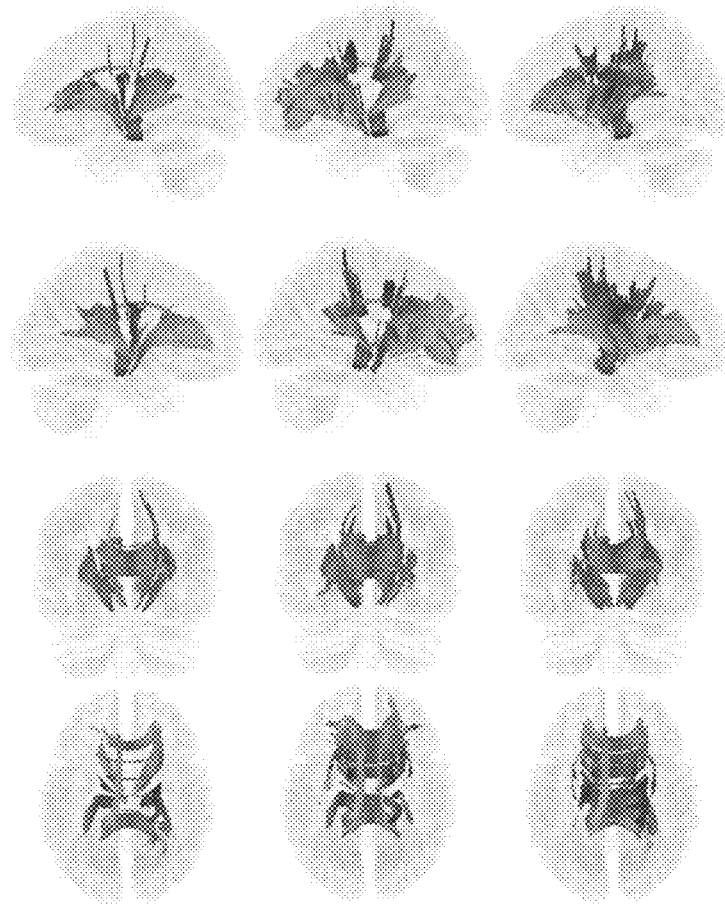
FIG. 8B provides scan and measurement data mapped by differential tractography for subject B, according to non-limiting embodiments or aspects.
Figure 8C:
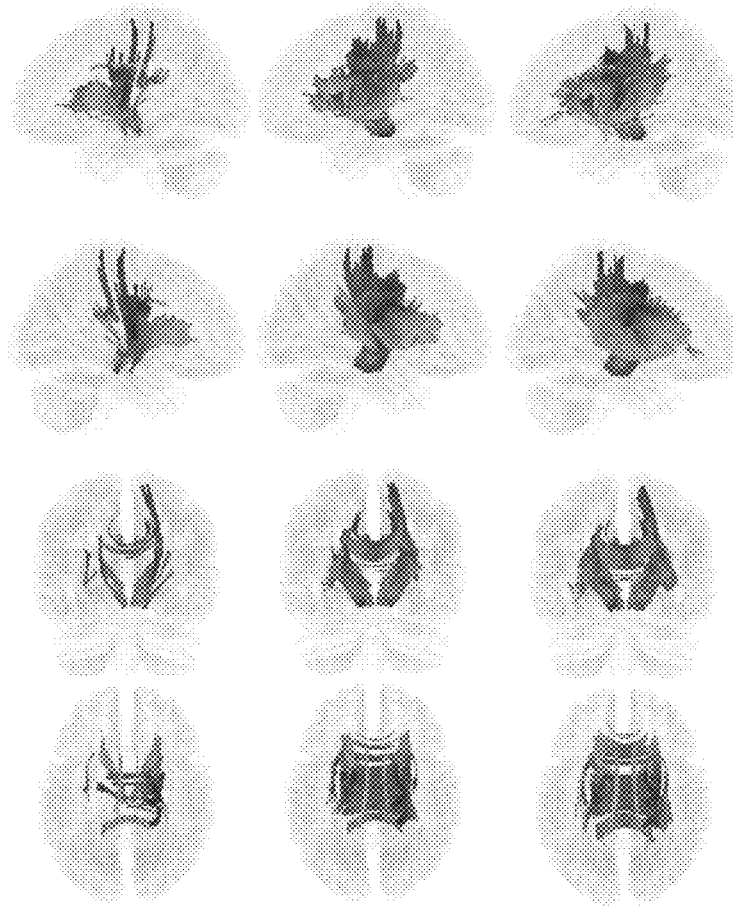
FIG. 8C provides scan and measurement data mapped by differential tractography for subject C, according to non-limiting embodiments or aspects.

With specific reference to FIGS. 8A-8C, subjects A, B, and C were selected to demonstrate a correlation based on their UHDRS TMS, in which higher deteriorating motor function was evident. Higher UHDRS TMS indicates worse performance, and all three subjects demonstrated an increased volume of affected tracts, likely correlating with decreased connectivity. This progression corresponded with UHDRS TMS higher scores at each measurement, with the exception of subject C, in which an increase in the volume of neurodegenerative tracts did not correspond with UHDRS TMS which remained unchanged at 6-months compared to the baseline scan.

Comparing Manifest and Premanifest Patients

Significant differences were observed in the manifest and premanifest group. Initial scans in symptomatic patients demonstrated using differential tractography to determine a significant number of affected bundles. This was in contrast to the demonstration of none or a small number of affected tracts using differential tractography in the premanifest group, as depicted in FIGS. 7A and 7B.

Longitudinal Analysis

With reference to FIGS. 9A and 9B, depicted is the outcome of a correlation analysis between tract volume and clinical scores in longitudinal data. Longitudinal data were examined in two analyses to determine the correlation between affected tract volumes and UHDRS. First, we studied the correlation between UHDRS clinical scores and tract volumes in each brain region (cingulum, corpus callosum, corticostriatal pathway, corticospinal pathway, and whole brain). Twenty-four of 35 correlations (68.571%) between tract volume and clinical scores showed statistical significance (p-value <0.05) and 10 correlations of 35 (28.571%) showed strong statistical significance (p-value <0.0001). Cingulum, corpus callosum, corticostriatal pathway, corticospinal pathway and whole brain significantly correlated (p-value <0.0001) with the UHDRS TMS, Dystonia Total (except in corticospinal pathway), Rapid Alternating Movements (RAM), Stroop Color-Word, and UHDRS Total Functional Capacity (TFC). A negative correlation was obtained for Dystonia Total, Chorea Total, and UHDRS Behavior (only in the corticospinal pathway).

With further reference to FIGS. 9A and 9B, a second longitudinal analysis examining the correlation of the change in clinical scores with the volume change of tracts was performed in all regions, cingulum, corpus callosum, corticostriatal pathway, corticospinal pathway and whole brain. 10 of 35 (28.571%) correlations showed statistical significance (p-value <0.05) and 7 of 35 correlations (20%) showed strong statistical significance (p-value <0.0001). Volume changes in cingulum significantly correlated with changes in the UHDRS Behavior (p-value <0.05). A strong statistical significance (p-value <0.0001) was also observed in relation to Dystonia Total and Rapid Alternating Movements. Dystonia Total (p-value between 0.05 and 0.0001 in all brain regions, except in the corticostriatal pathway) and RAM (p-value <0.0001 in all brain regions) were the clinical scores with the highest statistical significance. Results from this analysis support differential tractography as a strong biomarker for evaluating changes in volume of different brain regions in relation to clinical scores.

Cross-Sectional Analyses

With specific reference to FIGS. 10A-10D, provided are tables of a correlation analysis between tract volume and clinical scores in cross-sectional data. Cross-sectional data from scan 1, scan 2, and scan 3, was examined in two analyses. The first analysis evaluated the correlation between clinical scores and tract volumes in each scan. The second analysis evaluated the correlation between the changes in all clinical scores with the volume change in each scan. One hundred and five correlations were obtained for each analysis. In the first analysis, 4 of 105 results (3.809%) demonstrated statistical significance (p-value <0.05), and in the second analysis 8 of 105 results (7.619%) showed statistical significance (p-value <0.05).

The first of the two analyses conducted in manifest patients analyzed the correlation between clinical scores and tract volume and was subdivided into three independent analyses to evaluate correlation at three different time points (first, second, and third MRI scans). The first scan analysis demonstrated a negative correlation in cingulum in relation to the Stroop Color-Word. Analysis of the second scan yielded a positive correlation in cingulum in relation to UHDRS TMS and UHDRS TFC. Lastly, the third scan analysis showed a positive correlation in the corticostriatal pathway in relation to the UHDRS Behavior clinical score.

The second cross-sectional analysis was performed to evaluate the correlation between the changes in volumes of tracts and the changes in UHDRS clinical scores in manifest patients. The correlation was subdivided into three independent analyses to compared differences across scans. First, the changes from the first scan to the second scan showed a positive correlation in the cingulum, corpus callosum, corticospinal pathway, and whole brain when correlated to the change in scores of Dystonia Total. Second, the changes from the first scan to the third scan demonstrated a negative correlation in the cingulum when correlated to the change in scores of Stroop Color-Word, and positive correlation in the corpus callosum and corticostriatal pathway when correlated to the change in scores of RAM. Lastly, the changes from the second scan to the third scan showed a positive correlation in cingulum when correlated with the change in scores of UHDRS TFC.

Applications

We conducted correlation analyses between quantitative differential tractography measurements with clinical scores in manifest and premanifest HD patients. Overall results indicate that differential tractography is a robust dynamic monitoring biomarker with high statistical significance to determine changes in tract volumes of white matter tracts with the potential to supplement the UHDRS in manifest and premanifest HD. Differential tractography demonstrates to be a highly reliable monitoring biomarker to delimit changes exhibited in cingulum, corpus callosum, corticostriatal pathway, corticospinal pathway, and whole brain when correlated with UHDRS. Moreover, an increase of volume of damaged tracts was observed before symptom onset in one particular subject (see FIG. 8C). This prediction power can be of immense value to anticipate onset at the premanifest stage to characterize disease progression, adding great value and high reliability to differential tractography as a predictive monitoring biomarker. It is also noteworthy the distinction that differential tractography provides when comparing manifest and premanifest affected tracts measured by tract volume (as seen in FIGS. 7A and 7B). This distinction capacity corroborates the high reproducibility and accuracy of the technique. The use of differential tractography paired with a robust clinical evaluation at the pre-clinical stage in gene positive asymptomatic populations is of utmost clinical significance in routine clinical follow-up and when the assessment of the response of new treatment and therapies are required in clinical drug trials.

Implications of the Clinical Data

Longitudinal and cross-sectional analyses demonstrated the highest statistical correlation with the progression of clinical UHDRS scores in cingulum, corpus callosum, and corticostriatal pathway. These results further confirm the role of these white matter regions in HD progression. Demonstrated changes on differential tractography in both premanifest and manifest HD, and particularly in the earlier stages, is of high scientific value in longitudinal and cross-sectional studies. In premanifest HD, where clinical markers of disease progression do not exist, differential tractography can be used as a non-invasive tool to dynamically monitor clinically asymptomatic disease progression. In manifest HD, the observed progression made by differential tractography can be used to supplement existing clinical markers of progression.

Applicable Mechanisms

Degeneration in the association, commissural, and projection fibers are implicated in the course of Huntington's disease and its clinical manifestations. Degeneration in white matter tracts such as cingulum, corpus callosum, and corticostriatal pathways may be linked with changes in behavior, executive functions, movement, and the lack of integration of motor and cognitive functions resulting in progression of UHDRS TMS, RAM, Stroop Color Word, UHDRS TFC, and UHDRS Behavior scores. The high statistical significance exhibited by the corticospinal pathway in relation to UHDRS TMS, Stroop Color Word, TFC, and especially with RAM, reinforces the critical relationship between corticospinal tract demyelination and motor symptoms at the premanifest and manifest stages, which is highly correlated with progression of UHDRS motor scores. The highest correlation was found with respect to Dystonia Total and RAM in cross-sectional data studied by differential tractography, which is validated by the motor involvement of the disease. Therefore, differential tractography represents an innovative monitoring biomarker allowing detection of the exact anatomical location of degeneration and its subsequent correlation with loss of clinical function as measured by existing markers of progression.

Differential Tractography in Relation to Premanifest and Manifest Disease and UHDRS Scores In a relatively low number of patients, significant differences were observed between the premanifest and manifest HD. Relatively few areas were affected in premanifest patients in relation to patients in the manifest group (see FIGS. 7A and 7B), thereby lending further credibility to this imaging method. As expected, in manifest disease, significant progression was observed at 6 and 12 months in relation to the baseline scan. The observed increase in the volume of affected tracts on differential tractography corresponded with an increase in the UHDRS clinical scores. It will be appreciated that the UHDRS may be prone to variability. Differential tractography as an automated method is less prone to variability. In patients with manifest disease, differential tractography may supplement the use of the UHDRS. In premanifest patients, differential tractography may potentially demonstrate changes in white matter preceding the onset of the disease.

Further Applications

This study demonstrates the feasibility of using differential tractography as a monitoring biomarker to anticipate disease onset in premanifest and manifest HD. In manifest HD, differential tractography could demonstrate changes or progression at an anatomical level that may not be readily discernible with the UHDRS scores. Our findings confirmed the applicability of differential tractography as a dynamic non-invasive biomarker. Differential tractography has the potential to assess the efficacy of therapeutic trials and will be useful in patients with HD. This will be of particular use in patients with premanifest HD where future drug trials will be aimed to prevent progression to the manifest state.

Further Implementation

Figure 11:
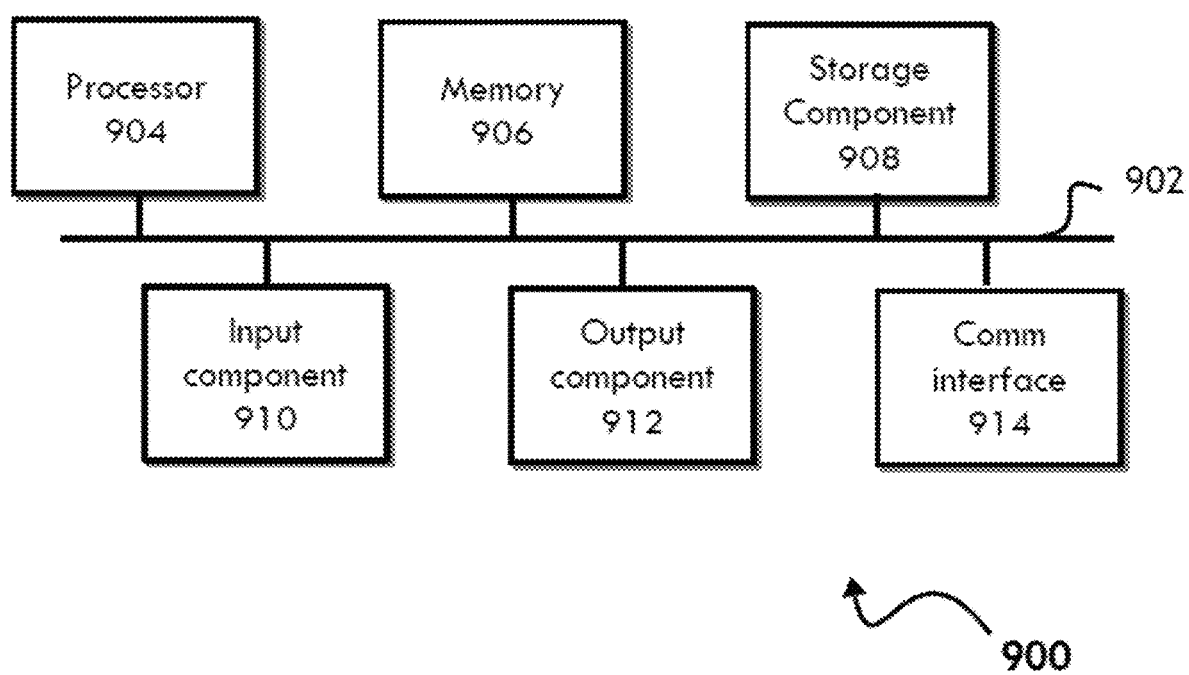
FIG. 11 provides a schematic of a computer or computing device for use in systems and methods for detecting neurodegeneration according to non-limiting embodiments or aspects.

As shown in FIG. 11, provided is a computing device 900 for use in systems and methods for detecting neurodegeneration using differential tractography. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 11, storage component 908 may store information and/or software related to the operation and use of device 900. For example, storage component 908 may include a hard disk and/or another type of computer-readable medium (e.g., a magnetic disk, an optical disk, a magneto-optic disk, a solid state disk, cloud storage, etc.). Input component 910 may include a component that permits device 900 to receive information, such as via user input (e.g., a touch screen display, a keyboard, a keypad, a mouse, a button, a switch, a microphone, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

The computing device 900 can be configured to execute instructions for performing the computer-implemented tasks described herein. Software can be one or more of an operating system (e.g., a Windows™ based operating system), browser application, client application, server application, proxy application, on-line service provider application, and/or private network application. The software, modules, algorithms, interfaces, etc. can be implemented by utilizing any suitable computer language or analytical system (e.g., C\C++, UNIX SHELL SCRIPT, PERL, JAVA™, JAVASCRIPT, HTML/DHTML/XML, FLASH, WINDOWS, UNIX/LINUX, APACHE, RDBMS including ORACLE, INFORMIX, and MySQL, PYTHON, R, LISP, or PROLOG). Commercial software suites for implementation of machine learning, among the other functions and modules described herein, include free, open-source, and proprietary software, such as, without limitation, lifelines, SAS, MATLAB, among many others.

Figure 12:
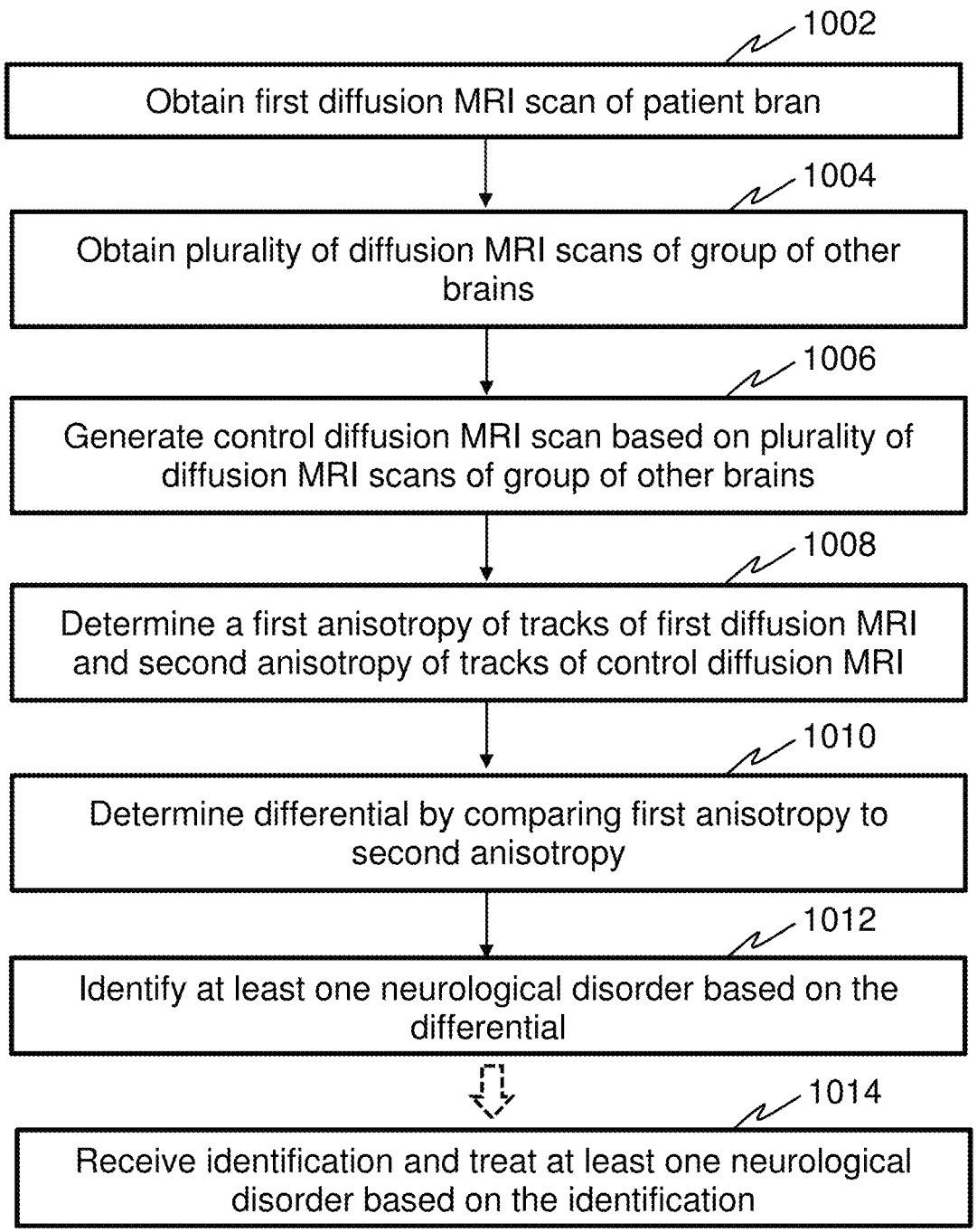
FIG. 12 provides a process diagram of a method for detecting neurodegeneration according to non-limiting embodiments or aspects.

With specific reference to FIG. 12, provided is a method for detecting neurodegeneration in a patient. The method may be executed by one or more computing devices as described in connection with FIG. 11. Any step of the described method may be performed by the same or different computing device as any other step. In step 1002, a computing device may obtain a first diffusion magnetic resonance imaging (MRI) scan of the brain of a patient. In step 1004, the computing device may obtain a plurality of diffusion MRI scans of a group of other brains. In step 1006, the computing device may generate a control diffusion MRI scan based on the plurality of diffusion MRI scans of the group of other brains. The control diffusion MRI scan may be generated based on an average of the plurality of diffusion MRI scans of the group of other brains. In step 1008, the computing device may determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement. The first anisotropy may be a measure of a segment of the first neural tracks having a length of at least 10 mm, and the second anisotropy may be a measure of a segment of the second neural tracks having a length of at least 10 mm. Alternatively or additionally, the first anisotropy may be a measure of a segment of the first neural tracks having a length of at least 50 mm, and the second anisotropy may be a measure of a segment of the second neural tracks having a length of at least 50 mm. The first anisotropy may include a value of spin density less than a value of spin density of the second anisotropy. The location of the first neural tracks may be in a cingulum region, a corpus callosum region, a corticostriatal pathway, or a corticospinal pathway of the brain of the patient, and the at least one neurological disorder may include Huntington's disease.

With further reference to FIG. 12, in step 1010, the computing device may determine a differential by comparing the first anisotropy to the second anisotropy. The differential may include at least a 15% difference of the first anisotropy from the second anisotropy. Alternatively or additionally, the differential may include at least a 30% difference of the first anisotropy from the second anisotropy. In step 1012, the computing device may identify at least one neurological disorder based on the differential and a location of the first neural tracks in the brain of the patient. In step 1014, the computing device may receive an identification of the at least one neurological disorder and treat, or trigger the treating of, the at least one neurological disorder.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:

1. A computer-implemented method for detecting neurodegeneration in a patient, comprising:
   obtaining, with at least one processor, a first diffusion magnetic resonance imaging (MRI) scan of the brain of the patient;
   obtaining, with at least one processor, a plurality of diffusion MRI scans of a group of other brains;
   generating, with at least one processor, a control diffusion MRI scan based on the plurality of diffusion MRI scans of the group of other brains;
   determining, with at least one processor, a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement;
   determining, with at least one processor, a differential by comparing the first anisotropy to the second anisotropy; and
   identifying, with at least one processor, at least one neurological disorder based on the differential and a location of the first neural tracks in the brain of the patient;
   wherein the differential comprises at least a 15% difference of the first anisotropy from the second anisotropy.

2. A system comprising at least one server computer including at least one processor, the at least one server computer programmed and/or configured to:
   obtain a first diffusion magnetic resonance imaging (MRI) scan of the brain of the patient;
   obtain a plurality of diffusion MRI scans of a group of other brains;
   generate a control diffusion MRI scan based on the plurality of diffusion MRI scans of the group of other brains;
   determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement;
   determine a differential by comparing the first anisotropy to the second anisotropy; and
   identify at least one neurological disorder based on the differential and a location of the first neural tracks in the brain of the patient;
   wherein the differential comprises at least a 15% difference of the first anisotropy from the second anisotropy.

3. A computer program product comprising at least one non-transitory computer-readable medium including program instructions that, when executed by at least one processor, cause the at least one processor to:
   obtain a first diffusion magnetic resonance imaging (MRI) scan of the brain of the patient;

obtain a plurality of diffusion MRI scans of a group of other brains;

generate a control diffusion MRI scan based on the plurality of diffusion MRI scans of the group of other brains;

determine a first anisotropy of first neural tracks of the first diffusion MRI scan and a second anisotropy of second neural tracks of the control diffusion MRI scan, wherein anisotropy is measured using an anisotropic spin distribution function and is a value of spin density of restricted anisotropic diffusion at a given diffusion orientation within a given displacement;

determine a differential by comparing the first anisotropy to the second anisotropy; and identify at least one neurological disorder based on the differential and a location of the first neural tracks in the brain of the patient;

wherein the differential comprises at least a 15% difference of the first anisotropy from the second anisotropy.

4. The method of claim 1, wherein the control diffusion MRI scan is generated based on an average of the plurality of diffusion MRI scans of the group of other brains.

5. The method of claim 1, wherein the first anisotropy is a measure of a segment of the first neural tracks having a length of at least 10 mm, and the second anisotropy is a measure of a segment of the second neural tracks having a length of at least 10 mm.

6. The method of claim 1, wherein the first anisotropy is a measure of a segment of the first neural tracks having a length of at least 50 mm, and the second anisotropy is a measure of a segment of the second neural tracks having a length of at least 50 mm.

7. The method of claim 1, wherein the differential comprises at least a 30% difference of the first anisotropy from the second anisotropy.

8. The method of claim 1, wherein the first anisotropy comprises a value of spin density less than a value of spin density of the second anisotropy.

9. The method of claim 1, wherein the location of the first neural tracks is in a cingulum region, a corpus callosum region, a corticostriatal pathway, or a corticospinal pathway of the brain of the patient, and wherein the at least one neurological disorder comprises Huntington's disease.

10. The system of claim 2, wherein the control diffusion MRI scan is generated based on an average of the plurality of diffusion MRI scans of the group of other brains.

11. The system of claim 2, wherein the first anisotropy is a measure of a segment of the first neural tracks having a length of at least 50 mm, and the second anisotropy is a measure of a segment of the second neural tracks having a length of at least 50 mm.

12. The system of claim 2, wherein the differential comprises at least a 30% difference of the first anisotropy from the second anisotropy.

13. The system of claim 2, wherein the first anisotropy comprises a value of spin density less than a value of spin density of the second anisotropy.

14. The system of claim 2, wherein the location of the first neural tracks is in a cingulum region, a corpus callosum region, a corticostriatal pathway, or a corticospinal pathway of the brain of the patient, and wherein the at least one neurological disorder comprises Huntington's disease.

15. The computer program product of claim 3, wherein the control diffusion MRI scan is generated based on an average of the plurality of diffusion MRI scans of the group of other brains.

16. The computer program product of claim 3, wherein the first anisotropy is a measure of a segment of the first neural tracks having a length of at least 50 mm, and the second anisotropy is a measure of a segment of the second neural tracks having a length of at least 50 mm.

17. The computer program product of claim 3, wherein the differential comprises at least a 30% difference of the first anisotropy from the second anisotropy.

18. The computer program product of claim 3, wherein the location of the first neural tracks is in a cingulum region, a corpus callosum region, a corticostriatal pathway, or a corticospinal pathway of the brain of the patient, and wherein the at least one neurological disorder comprises Huntington's disease.

19. A method of treating a neurological disorder in a patient, comprising:
receiving, from a computing device comprising the computer program product of claim 3, an identification of the at least one neurological disorder; and
treating, based on the identification, the at least one neurological disorder.

20. The method of claim 19, wherein the neurological disorder is Huntington's Disease.

21. The method of claim 20, wherein the differential of the first neural tracks in the brain of the patient is measured in the cingulum, corpus callosum, corticostriatal pathway, corticospinal pathway, or whole brain of the patient.

* * * * *